United States Patent
Chow et al.

(10) Patent No.: US 10,201,523 B2
(45) Date of Patent: Feb. 12, 2019

(54) USE OF WILFORLIDE A FOR OVERCOMING CHEMOTHERAPY RESISTANCE

(71) Applicant: WESTERN UNIVERSITY OF HEALTH SCIENCES, Pomona, CA (US)

(72) Inventors: Moses Sing Sum Chow, Chino Hills, CA (US); Ying Huang, Arcadia, CA (US); Zhi Jun Wang, Chino Hills, CA (US)

(73) Assignee: WESTERN UNIVERSITY OF HEALTH SCIENCES, Pomona, CA (US)

( * ) Notice: Subject to any disclaimer, the term of this patent is extended or adjusted under 35 U.S.C. 154(b) by 0 days.

(21) Appl. No.: 14/915,965

(22) PCT Filed: Sep. 12, 2014

(86) PCT No.: PCT/US2014/055401
§ 371 (c)(1),
(2) Date: Mar. 2, 2016

(87) PCT Pub. No.: WO2015/038896
PCT Pub. Date: Mar. 19, 2015

(65) Prior Publication Data
US 2016/0199345 A1    Jul. 14, 2016

Related U.S. Application Data

(60) Provisional application No. 61/877,353, filed on Sep. 13, 2013.

(51) Int. Cl.
| A61K 31/365 | (2006.01) |
| A61K 31/704 | (2006.01) |
| A61K 31/517 | (2006.01) |
| A61K 31/337 | (2006.01) |
| A61K 45/06 | (2006.01) |
| A61K 36/37 | (2006.01) |

(52) U.S. Cl.
CPC .......... *A61K 31/365* (2013.01); *A61K 31/337* (2013.01); *A61K 31/517* (2013.01); *A61K 31/704* (2013.01); *A61K 36/37* (2013.01); *A61K 45/06* (2013.01)

(58) Field of Classification Search
CPC .. A61K 31/365; A61K 31/704; A61K 31/517; A61K 31/337
USPC ...................... 514/34, 266.24, 468
See application file for complete search history.

(56) References Cited

U.S. PATENT DOCUMENTS

| 8,357,690 B2 | 1/2013 | Armstrong et al. |
| 2012/0122825 A1 | 5/2012 | Karlin et al. |
| 2012/0308567 A1 | 12/2012 | Fukuoka et al. |

FOREIGN PATENT DOCUMENTS

| CA | 2093866 A1 | 10/1993 |
| CN | 102443039 A | 5/2012 |
| CN | 101991633 B | 11/2012 |
| JP | 2005330253 A | 12/2005 |
| WO | 2014/031543 A1 | 2/2014 |
| WO | 2015/038896 A2 | 3/2015 |

OTHER PUBLICATIONS

Wamg et al. Various Monomers of Tripterygium wilfordii Effecting Adenosine Deaminase Activity and Inducing HL-60 Cell Apopotosis. Fudan Univ J Med Sci 34(1):107-110, 2007. (Abstract only).*
Davy et al. Total blood volume in healthy young and older men. J. Appl. Physiol. 76(5):2059-2062, 1994.*
Minelli et al. 2-Chloroadenosine Modulates PAR-1 and IL-23 Expression and Enhances Docetaxel Effects on PC3 Cells. Prostate 68:360-372, 2008. (Year: 2008).*
Khan et al. The Evolving Role of Docetaxel in the Management of Androgen Independent Prostate Cancer. Journal of Urology 170:1709-1716, 2003. (Year: 2003).*
International Search Report and Written Opinion of corresponding International Application No. PCT/US2014/055401, dated Nov. 14, 2014.
International Preliminary Report on Patentability of corresponding International Application No. PCT/US2014/055401, dated Mar. 15, 2016.
Feng et al., "Molecular and Cellular Mechanism Studies on Anti-cancer Effects of Chinese Medicine", Biomedical Engineering, Trends, Research and Technologies, Jan. 8, 2011, pp. 332-362.
Xue et al., "Comparative study on the anti-inflammatory and immune suppressive effect of Wilforide A", Fitoterapia, 2010, vol. 81; pp. 1109-1112.
English abstract of CN 101991633, Nov. 7, 2012.
English abstract of CN 102443039, May 9, 2012.
Extended European Search Report in Application No. 14843285.9, dated Feb. 16, 2017.
Fidler et al., "PG490-88, a derivative of triptolide, causes tumor regression and sensitizes tumors to chemotherapy", Molecular Cancer Therapeutics, American Association of Cancer Research, vol. 2, No. 9, 2003, pp. 855-862.

(Continued)

*Primary Examiner* — Yih-Horng Shiao
(74) *Attorney, Agent, or Firm* — J.A. Lindeman & Co., PLLC

(57) ABSTRACT

The invention provides compositions comprising wilforlide A for overcoming drug resistance in cancer therapy, particularly in the treatment of cancers which have exhibited resistance to treatment by chemotherapeutic drugs. Methods and compositions for treating a cancer are disclosed. The method administers to a patient in need thereof a combination of wilforlide A and a chemotherapeutic drug. Wilforlide A and chemotherapeutic drug are administered in a combined amount effective to treat the cancer. The cancer being treated is at least in part resistant to treatment by the chemotherapeutic drug alone.

5 Claims, 12 Drawing Sheets

(56) References Cited

OTHER PUBLICATIONS

Luo et al., "Simple method for determination of five terpenoids from different parts of Tripterygium wilfordii and its preparations by HPLC coupled with evaporative light scattering detection", J. Sep. Sci., 2007, 30, pp. 1284-1291.

Wenlin Xu et al., "Modulation of P-glycoprotein expression by triptolide in adriamycin-resistant K562/A02 cells", Oncology Letters 3, 2012, pp. 485-489.

Ravula et al., "Bioassay-guided identification of novel P-glycoprotein inhibitors from traditional Chinese medicines", Abstract, Apr. 2010, Cancer Res. vol. 70, Suppl. 8: Abstract nr. 1534.

Ravula et al., "Extract of Tripterygium wirfordii sensitized drug resistant prostate cancer cells to docetaxel", Abstract nr. 1124364; J. Clin. Pharmacol., 2011, 51:1364.

\* cited by examiner

USE OF WILFORLIDE A FOR OVERCOMING CHEMOTHERAPY RESISTANCE

FIELD OF THE INVENTION

The invention relates to the use of wilforlide A to enhance the effectiveness of chemotherapeutic drugs.

BACKGROUND

Drug resistance invariably develops over the course of continuing chemotherapy. Overcoming this problem is a major challenge in the treatment of cancer. Indeed, tumor cells utilize multiple mechanisms to increase their resistance to chemotherapeutic drugs. For example, tumor cells may overexpress the multiple drug resistant transporter and oncoprotein epidermal growth factor receptor genes, as well as induce the activity of NF-E2-related factor 2, a redox-sensing transcription factor that upregulates a wide spectrum of genes involved in glutathione metabolism and drug detoxification. See (Huang et al., 2005a; Makarovskiy et al., 2002; Wang et al., 2010); (Salzberg et al., 2007; Sirotnak et al., 2000); (Singh et al., 2010; Zhang et al., 2010); and (Huang and Sadee, 2003; Seruga et al., 2010). The Hedgehog pathway is another cell signaling pathway that is involved in chemoresitance. (Domingo-Domenech et al., 2012).

To date, no single agent that was designed to target a specific mechanism of resistance has been found to be effective. However, the small molecule, wilforlide A, which can be extracted from the Chinese medicinal herb, *Tripterygium wilfordii*, sensitizes cancer cells that have become resistant to chemotherapeutic drug therapy, so that the cancer once again becomes sensitive to the chemotherapeutic drug.

SUMMARY OF THE INVENTION

The invention relates to methods of treating a patient suffering from cancer, that has acquired resistance to a chemotherapeutic drug, by coadministering wilforlide A in combination with the chemotherapeutic drug. Thus, the method administers to a patient in need thereof a combination of wilforlide A and a chemotherapeutic drug. The invention also relates to compositions of wilforlide A, either of wilforlide A only, or in combination with a chemotherapeutic drug. Types of chemotherapeutic drugs that the methods and compositions of the invention can be used to overcome drug resistance include topoisomerase drugs, taxanes, and dual tyrosine kinase inhibitors.

Generally, it is to be understood herein that cancer being treated by a method or composition of the invention is at least in part resistant to treatment by the chemotherapeutic drug alone. Therefore, methods of the invention coadminister wilforlide A in a dosage amount that increases a chemotherapeutic drug's efficacy as compared to the efficacy of the chemotherapeutic drug when administered alone. The methods of treatment and compostions of the invention can be used to treat solid and haematological tumors of various organs, including breast, blood and prostate cancers Wilforlide A and a chemotherapeutic drug may be administered sequentially or co-administered. When they are administer sequentially, at least a portion of wilforlide A is administered prior to administration of a chemotherapeutic drug. Wilforlide A may be administered in the same manner and using a similar or the same chemotherapeutic composition. As noted above, in a method of the invention wilforlide A and a chemotherapeutic drug may be co-administered and that may be in a single composition containing both wilforlide A and the chemotherapeutic drug. Accordingly, another embodiment of the invention relates to a chemotherapeutic composition comprising a combination of wilforlide A and a chemotherapeutic drug, wherein wilforlide A and the chemotherapeutic drug are administered in a combined amount effective to treat the cancer; and a pharmaceutically acceptable carrier.

Brief Description of the Tables

Table 1 provides the results of a sulforhodamine B (SRB) cell viability assay of a 72 hour-long wilforlide A dose-response analysis used to determine the $IC_{50}$ of wilforlide A in the docetaxel-resistant prostate cancer cell line PC3-TxR. Table 1 correlates with FIG. 1.

Table 2 provides the concentrations of docetaxel, lapatinib, and daunodubicin and the cell lines that were used to determine the $IC_{50}$ concencentrations for these drugs.

Table 3 provides the results of the $IC_{50}$ concentrations of docetaxel, daunorubicin, and lapatinib in the absence and presence of wilforlide pretreatment.

Table 4 reports the results of an SRB cell viability assay of docetaxel-sensitive PC3 cells that were pretreated with 0.6 µg/ml of wilforlide A, followed by 72 hours of treatment with various concentrations of docetaxel. Tables 4 and 5 correlate with FIG. 2A.

Table 5 reports the results of an SRB cell viability assay of docetaxel-sensitive PC3 cells after 72 hours of treatment with various concentrations of docetaxel and no wilforlide A pretreatment.

Table 6 reports the results of an SRB cell viability assay of docetaxel-sensitive PC3 cells that were pretreated with 1.25 µg/ml of wilforlide A, followed by 72 hours of treatment with various concentrations of docetaxel. Tables 6 and 7 correlate with FIG. 2B.

Table 7 reports the results of an SRB cell viability assay of docetaxel-sensitive PC3 cells after 72 hours of treatment with various concentrations of docetaxel and no wilforlide A pretreatment.

Table 8 reports the results of an SRB cell viability assay of docetaxel-sensitive PC3 cells that were pretreated with 2.5 µg/ml of wilforlide A, followed by 72 hours of treatment with various concentrations of docetaxel. Tables 8 and 9 correlate with FIG. 2C.

Table 9 reports the results of an SRB cell viability assay of docetaxel-sensitive PC3 cells after 72 hours of treatment with various concentrations of docetaxel and no wilforlide A pretreatment.

Table 10 reports the results of an SRB cell viability assay of docetaxel-resistant PC3-TxR cells that were pretreated with 0.6 µg/ml of wilforlide A, followed by 72 hours of treatment with various concentrations of docetaxel. Tables 10 and 11 correlate with FIG. 3A.

Table 11 reports the results of an SRB cell viability assay of docetaxel-resistant PC3-TxR cells after 72 hours of treatment with various concentrations of docetaxel and no wilforlide A pretreatment.

Table 12 reports the results of an SRB cell viability assay of docetaxel-resistant PC3-TxR cells that were pretreated with 1.25 µg/ml of wilforlide A, followed by 72 hours of treatment with various concentrations of docetaxel. Tables 12 and 13 correlate with FIG. 3B.

Table 13 reports the results of an SRB cell viability assay of docetaxel-resistant PC3-TxR cells after 72 hours of treatment with various concentrations of docetaxel and no wilforlide A pretreatment.

Table 14 reports the results of an SRB cell viability assay of docetaxel-resistant PC3-TxR cells that were pretreated with 2.5 µg/ml of wilforlide A, followed by 72 hours of treatment with various concentrations of docetaxel. Tables 14 and 15 correlate with FIG. 3C.

Table 15 reports the results of an SRB cell viability assay of docetaxel-resistant PC3-TxR cells after 72 hours of treatment with various concentrations of docetaxel and no wilforlide A pretreatment.

Table 16 reports the results of an SRB cell viability assay of docetaxel-resistant PC3-TxR cells that were pretreated with 5.0 µg/ml of wilforlide A, followed by 72 hours of treatment with various concentrations of docetaxel. Tables 16 and 17 correlate with FIG. 3D.

Table 17 reports the results of an SRB cell viability assay of docetaxel-resistant PC3-TxR cells after 72 hours of treatment with various concentrations of docetaxel and no wilforlide A pretreatment.

Table 18 reports the results of an SRB cell viability assay of docetaxel-resistant DU145-TxR cells that were pretreated with 2.5 µg/ml of wilforlide A, followed by 72 hours of treatment with various concentrations of docetaxel. Tables 18 and 19 correlate with FIG. 4

Table 19 reports the results of an SRB cell viability assay of docetaxel-resistant DU145-TxR cells after 72 hours of treatment with various concentrations of docetaxel and no wilforlide A pretreatment.

Table 20 reports the results of an SRB cell viability assay of daunorubicin-resistant K562/Dox cells that were pretreated with 2.5 µg/ml of wilforlide A, followed by 72 hours of treatment with various concentrations of docetaxel. Tables 20 and 21 correlate with FIG. 5.

Table 21 reports the results of an SRB cell viability assay of daunorubicin-resistant K562/Dox cells after 72 hours of treatment with various concentrations of docetaxel and no wilforlide A pretreatment.

Table 22 reports the results of an SRB cell viability assay of lapitinib-resistant, HER2-positive, breast adenocarcinoma SkBr3-TxR cells that were pretreated with 2.5 µg/ml of wilforlide A, followed by 72 hours of treatment with various concentrations of docetaxel. Tables 22 and 23 correlate with FIG. 6.

Table 23 reports the results of an SRB cell viability assay of lapitinib-resistant, HER2-positive, breast adenocarcinoma SkBr3-TxR cells after 72 hours of treatment with various concentrations of docetaxel and no wilforlide A pretreatment.

Table 24 reports the results of an SRB cell viability assay of lapitinib-resistant, HER2-positive, breast ductal carcinoma Bt474-TxR cells that were pretreated with 2.5 µg/ml of wilforlide A, followed by 72 hours of treatment with various concentrations of docetaxel. Tables 24 and 25 correlate with FIG. 7A.

Table 25 reports the results of an SRB cell viability assay of lapitinib-resistant, HER2-positive, breast ductal carcinoma Bt474-TxR cells after 72 hours of treatment with various concentrations of docetaxel and no wilforlide A pretreatment.

Table 26 reports the results of an SRB cell viability assay of lapitinib-resistant, HER2-positive, breast ductal carcinoma Bt474-TxR cells that were pretreated with 25 µg/ml of wilforlide A, followed by 72 hours of treatment with various concentrations of docetaxel. Tables 24 and 25 correlate with FIG. 7B.

Table 27 reports the results of an SRB cell viability assay of lapitinib-resistant, HER2-positive, breast ductal carcinoma Bt474-TxR cells after 72 hours of treatment with various concentrations of docetaxel and no wilforlide A pretreatment.

DETAILED DESCRIPTION

Figure 1:
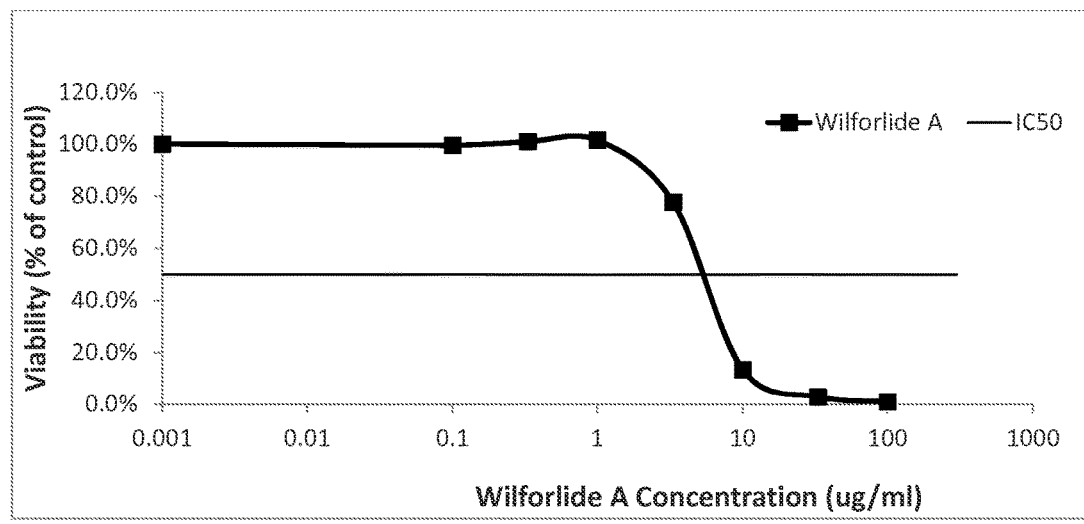
FIG. 1 shows sulforhodamine B (SRB) cell viability assay results from 72 hour long wilforlide A dose-response assay used to determine the $IC_{50}$ of wilforlide A in the docetaxel-resistant prostate cancer cell line PC3-TxR. See Table 1.

Described herein are methods of treating a patient suffering from cancer that has acquired a resistance to a chemotherapeutic agent that, if not for the acquired resistance, could be used to effectively treat the patient. More particularly, methods of treatment according to the invention coadminister a dose of the small molecule compound 3-epiabruslactone A with a chemotherapeutic drug to which the cancer being targeted by the method of treatment has become resistant.

Herein, 3-epiabruslactone A will generally be referred to by its common name, wilforlide A. Wilforlide A, which has the molecular formula, $C_{30}H_{46}O_3$, and a molecular weight of 454.684, can be synthesized or extracted from a plant source. For example, wilforlide A can be extracted with organic solvents from the root bark or xylem of Tripterygium wilfordii, a medicinal plant that is indigenous to China. See Luo et. al, *J. Sep. Sci.* 30(9):1284-91 (2007), which is included in its entirety herein. Wilforlide A sensitizes cancer cells that have become resistant to chemotherapeutic drug therapy, so that the cancer once again becomes sensitive to the chemotherapeutic drug.

In various embodiments, methods of the invention overcome anti-cancer chemotherapeutic drug resistance by contacting a chemotherapeutic drug-resistant cancer cell with wilforlide A, and effect a reversal of the cell's resistance to chemotherapeutic drug, thereby allowing the chemotherapeutic drug to cause the drug-resistant cancerous cell's death or cytostasis. Thus, methods of treatment of the invention are used to inhibit, retard or prevent growth of tumor cells that are resistant to a chemotherapeutic agent.

As used herein, the term "treating" or "treatment" refers to coadministering wilforlide A with a chemotherapeutic drug to a subject that has cancer that is resistant to treatment with the chemotherapeutic drug, with the purpose to cure, heal, alleviate, relieve, alter, remedy, ameliorate, improve, or affect cancer. In various embodiments, the method of the invention administers wilforlide A and the chemotherapeutic drug that is co-administered with wilforlide A at the same time or in immediate succession, while in other embodiments, wilforlide A is administered prior to the administration of the chemotherapeutic drug to allow the cells of the cancer that is being treated to become at least partially sensitized by wilforlide A prior to being contacted with the chemotherapeutic drug. It is to be understood herein that methods of the invention accomodate flexible and active regimens for combining wilforlide A and chemotherapeutic drugs.

"An effective amount" of wilforlide A, as understood herein, refers to the amount of wilforlide A that is required to confer a reduction in the resistance of the cancer cells to a designated chemotherapeutic drug. Effective amounts may vary, as recognized by those skilled in the art, depending on route of administration, excipient usage, and the possibility of co-usage with other agents.

The dosage amount of wilforlide A administered to a patient according to a method of the invention is sufficient to reverse the resistance of a cancer to a chemotherapeutic drug that is coadministered with wilforlide A. In various embodiments, the dose of wilforlide A administered by a method of the invention is between 0.5 and 40 mg of wilforlide A/kg of body weight. For example, in one embodiment, a method of the invention administers about 1.2 mg/kg of wilforlide A, while in another embodiment, a method of the invention administers 6 mg/kg, and in yet another embodiment, a method of the invention administers 30 mg/kg.

Cancers that can be treated by methods of the invention include both solid and haematological tumors of various organs. Nonlimiting examples of solid tumors are metastatic breast cancer, and prostate cancer, including androgen-dependent and androgen-independent prostate cancer. Haematolgical tumors that are treatable by the methods of the invention include, for example, chronic myelogenous leukemia (CML), which is characterized by abnormal proliferation of immature granulocytes, for example, neutrophils, eosinophils and basophils, in the blood, bone marrow, the spleen, liver and sometimes in other tissues.

Chemotherapeutic drugs that may be coadministered with wilforlide A in methods of treating cancer according to the invention include topoisomerase inhibitors, such as, for example daunorubicin hydrocholoride. Therefore, in a various embodiment, the cancer treated by a method of the invention has been sensitized to topoisomerase inhibitors, e.g., the subject has received radiation and/or the subject has received a phosphatase inhibitor (e.g., okadiac acid) prior to the administration of the CDP-topoisomerase inhibitor conjugate, particle or composition. In one embodiment, the cancer is sensitized or has been sensitized to topoisomerase inhibitors and the cancer is a breast cell cancer, while in another embodiment the cancer is a prostate cancer, and in yet another embodiment, the cancer is a leukemia.

In various embodiments, methods of the invention coadminister wilforlide A with 25 to 45 $mg/m^2$/day of intravenously (IV)-administered daunorubicin hydrocholoride on days 1, 2, and 3 of a first cycle of treatment (i.e., course of treatment), and on days 1, 2 of subsequent cycles.

Other chemotherapeutic drugs that can be coadministered with wilforlide A in methods of treating cancer according to the invention are anti-mitotic taxoid drugs, also called taxanes, such as docetaxel (Taxotere™). In one embodiment, the cancer is sensitized or has been sensitized to a taxane and the cancer is a breast cell cancer, while in another embodiment the cancer is a prostate cancer, and in yet another embodiment, the cancer is a leukemia.

In various embodiments, methods of the invention coadminister wilforlide A with 50 to 80 $mg/m^2$/day of intravenously (IV)-administered docetaxel hydrate every three weeks for one to ten cycles. In other embodiments of the invention, 50 to 80 $mg/m^2$/day of intravenously (IV)-administered docetaxel hydrate is administered once a day over an interval of 3 to 4 weeks (the dose may be appropriately increased or decreased).

Methods of the invention also accomodate treatment using dual tyrosine kinase inhibitors (TKI) which interrupts the HER2/neu and epidermal growth factor receptor (EGFR) pathways such as lapatinib, which is commercially available under the trade name, Tykerb®. Therefore, patients which may advantageously be treated by methods of the invention include the following patient populations: (a) TKI naive cancer patients, wherein the treatment provides prevention or delay of resistance to TKI treatment, (b) patients with tumors expressing the wild-type EGFR, (c) patients with tumors expressing mutated forms of the EGFR, (d) patients previously treated with EGFR inhibitors, such as gefitinib or erlotinib afatinib, dacomitinib or others wherein the treatment provides to overcome primary or acquired resistance to EGFR inhibitors (e) patients with acquired resistance to treatment with TKIs such as gefitinib or erlotinib, afatinib, dacomitinib or others wherein the treatment provides to overcome resistance to TKI treatment, (g) patient populations with primary or acquired resistance caused by T790M (T790M+), wherein the i treatment provides to prevent or overcome resistance to TKI treatment, and (h) patient populations with primary or acquired resistance not caused by T790M (T790M-), e.g. by other mechanisms such as MET oncogene or by unknown origin, wherein the treatment provides to prevent or overcome resistance to TKI treatment.

A preferred dose of lapatinib ditosylate to be coadministered with wilforlide A is 1,250 mg (five tablets) administered orally once daily for 21 days in combination with capecitabine 2,000 mg/m2/day (administered orally in two doses approximately 12 hours apart) on days 1-14 in a 21-day cycle.

The invention also relates to pharmaceutical compositions of wilforlide A. Therefore, in various embodiments, wilforlide A-containing compositions of the invention are chemotherapeutic compositions for use in treating patients suffering from cancer. In an embodiment, a chemotherpeutic composition includes wilfolide A, and does not include another chemotherapeutic drug component. In such an embodiment, the dose of wilforlide A is sufficient to overcome resistance of a patient to the chemotherapeutic drug, wherein the dose of wilforlide A is not cytotoxic. In other embodiments, however, chemotherapeutic compositions of the invention include a combination of wilforlide A and a chemotherapeutic drug. As with wilforlide A-only compositions, the dose of wilforlide A is sufficient to overcome resistance of a patient to the chemotherapeutic drug, but is not a cytotoxic dose.

As stated above, the dose of wilforlide A contained in either the wilforlide A-only composition or wilforlide A combination compositions is sufficient to overcome resistance of a patient to the chemotherapeutic drug. A sufficient dose of wilforlide A may vary over the course of a flexible and active treatment regimen. In various embodiments, the dose of wilforlide A contained in a chemotherapeutic composition of the invention is from 50 to 500 μg/ml of a liquid composition formulated for IV administration.

Examples of combination chemotherapeutic compositions of the invention, include compositions in which wilforlide A is combined with topoisomerase inhibitors, with taxane compounds, or with dual tyrosine kinase inhibitors (TKI) which interrupts the HER2/neu and epidermal growth factor receptor (EGFR) pathways. In various embodiments, a combined chemotherapeutic composition of the invention may combine wilforlide A with the topoisomerase inhibitor, daunorubicin hydrocholoride. In other embodiments, a combined chemotherapeutic composition of the invention may combine wilforlide A with the taxane compound, docetaxel hydrate. In yet another embodiment, a combined chemotherapeutic composition of the invention may combine wilforlide A with the TKI, lapatinib ditosylate.

The aforementioned compositions can be administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In various embodiments, the chemotherapeutic compositions of the invention, including wilforlide A-only compositions and compositions of combinations of wilforlide A and another chemotherapeutic drug are formulated and administered according to the formulations and methods of administration that are known in the art for chemotherapeutic drugs that are administered in combination with wilforlide A.

Compositions for oral administration can also be any orally acceptable dosage form including, but not limited to, capsules, tablets, emulsions and aqueous suspensions, dispersions and solutions. In the case of tablets for oral use, carriers that are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents.

Compositions of the invention may also contain one or more excipients. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

The compositions of the invention accomodate various excipient emulsifiers to enhance the bioavailibilty of wilforlide A, including hydropropyl β cyclodextrin (HBCD, Roquette America, Keokuk, Iowa) and mono-, di- and triglyceride emulsifiers, such as, for example emulsifiers sold commercially as Capmul™ line of products (ABITEC Corp.) In some embodiments, a composition may contain wilforlide A combined with a monoglyceride emulsifier, a diglyceride emulsifier, a triglyceride emulsifier, or a combination thereof at a concentration of (wilforlide A/emulsifier) chosen from 0.5 to 5 mg/ml. In one embodiment, the concentration of (wilforlide A/emulsifier) is 3 mg/ml.

EXAMPLES

Example 1

The determination of the wilforlide A $IC_{50}$. The $IC_{50}$ for wilforlide A was determined in vitro for the purpose of identifying wilforlide A concentrations that could be used for determining its chemosensitizing effect (CE) in cell cultures of the docetaxel-resistant prostate cancer line PC3-TxR (Obtained from Prof. Evan T. Keller, University of Michigan). The PC3-TxR cultures were prepared by adding 3000 cells suspended in 100 μl of medium to each well of flat-bottom Cellstar® 96 well cell culture plates with lids (Cat #655180, Purchased from Greiner Bio-one, Monroe, N.C.). The cell medium was a base RPMI 1640 medium supplemented with 10% fetal bovine serum (Thermo Scientific, Logan, Utah) and a solution of penicillin (100 U/ml) and streptomycin (100 μg/ml) (Life Technologies Grand Island, N.Y.). Septuplicate wells were assigned to each experimental condition tested (i.e., n=3 for each data point), and a 24 hour recovery period for the cells following the seeding of the wells was allowed. During the recovery period, the cells were incubated at 37° C. and 5% $CO_2$.

Post-recovery, the plating media was aspirated from the cell cultures, and replaced with 50 μl per well of RPMI containing a designated concentration of wilforlide A. Then, the cells were incubated in the presence of the wilforlide A media for 72 hours. The 50 μl wilforlide A aliquots were prepared by making 1:3 serial dilutions of a wilforlide A stock solution (0.5 mg/ml in DMSO) to with concentrations ranging from $1\times10^2$ to $1\times10^{-3}$ μg/ml.

Following the 72 hour wilforlide A treatment, a sulforhodamine B (SRB) assay was used to quantitate living cells. To perform the assay, the wilforlide A media was aspirated from each well, and replaced with a 10% solution of cold trichloroacetic acid (TCA) (Cat #: T6399, purchased from Sigma-Aldrich), and incubated for one hour at 4° C. After the TCA incubation, the TCA solution was aspirated, and the cells were washed five times with tap water. After removing the last wash, the plates were left with lids off at room temperature until the surfaces were dry, which took one to two hours. Then 50 μl of a 0.4% solution of sul-forhodamine B (SRB) sodium salt (Cat #: S9012, purchased from Sigma-Aldrich) was added to each well and the plates were incubated at room temperature for 20 to 30 minutes. Afterwards, the wells were washed five times with a 1% acetic acid solution in 10 mM TRIS base (Cat #: 161-0719, purchased from Bio-Rad Laboratories, Hercules, Calif.). The plates were subsequently left to dry for several hours or overnight. SRB that remained in the dried wells was solubilized by adding 100 µl of SRB solubilization solution (10 mM TRIS base) to each well, and placing the plates either on a gently-moving shaker or letting the plates remain stationary at room temperature until the SRB dissolves, which takes about five to ten minutes. The amount of SRB in each well, which correlated directly to the number of living cells at fixation, was determined spectrophotometrically at an absorbance of 565 nm by a microplate reader. The cell viability results for the wilforlide A dose response analysis described in this Example are presented in Table 1, and in graphical form in FIG. 1.

adenocarcinoma line SkBr3 and its lapatinib-resistant subline, SkBr3-TxR (Obtained from Prof. Xiaojiang Cui, Cedars-Sinai, Beverly Hills, Calif.).

To obtain the $IC_{50}$ values, the desired cells were plated into sterile, F-bottom Cellstar™ 96 well cell culture plates with lids (Cat #655180, Purchased from Greiner Bio-one, Monroe, N.C.) by placing into each well, 100 µl of medium containing 3000 cells (for PC3, PC3-TxR, DU145, DU-145-TxR) or 5000 cells (for K562, K562/Dox, BT474, BT474-TxR, SkBr3 and SkBr3-TxR) in RPMI 1640 supplemented with 10% fetal bovine serum (Thermo Scientific, Logan, Utah) and a solution of penicillin (100 U/ml) and streptomycin (100 µg/ml) (Life Technologies Grand Island, N.Y.). Triplicate wells were assigned to each experimental condition tested, and a 24 hour recovery period for the cells following the seeding of the wells was allowed. During the recovery period, the cells were incubated at 37° C. and 5% $CO_2$.

TABLE 1

| Wilforlide A (µg/ml) | 100 | 33.3 | 10 | 3.33 | 1 | 0.333 | 0.1 | 0.001 |
|---|---|---|---|---|---|---|---|---|
| A at 565 nm | 0.023 | 0.096 | 0.399 | 2.082 | 2.626 | 2.645 | 2.611 | 2.599 |
| (in triplicate) | 0.024 | 0.072 | 0.358 | 1.928 | 2.629 | 2.618 | 2.592 | 2.624 |
| background = 0.044 | 0.023 | 0.074 | 0.348 | 2.081 | 2.755 | 2.661 | 2.610 | 2.607 |
|  | 0.033 | 0.073 | 0.325 | 1.950 | 2.658 | 2.646 | 2.592 | 2.635 |
|  | 0.027 | 0.069 | 0.320 | 2.070 | 2.659 | 2.664 | 2.617 | 2.593 |
|  | 0.018 | 0.072 | 0.357 | 2.088 | 2.616 | 2.617 | 2.615 | 2.646 |
| mean A | 0.025 | 0.076 | 0.351 | 2.033 | 2.657 | 2.642 | 2.606 | 2.618 |
| SD | 0.005 | 0.010 | 0.028 | 0.074 | 0.051 | 0.020 | 0.011 | 0.021 |
| % viable | 1.0 | 2.9 | 13.4 | 77.7 | 101.5 | 100.9 | 99.6 | 100.0 |
| CV | 20.06 | 13.03 | 8.08 | 3.61 | 1.92 | 0.77 | 0.43 | 0.80 |

Example 2

A comparison of chemosensitization effect (CE) values for wilforlide A in the context of various different chemotherapeutic drugs and cancer cell lines. In these comparisons, the in vitro $IC_{50}$ of a tested chemotherapeutic drug (D) in cell culture was compared to the drug's $IC_{50}$ when drug treatment followed pretreatment of the cells with wilforlide A (Purchased from PI & PI Technology Inc. of Guangzhou, China or the National Institutes for Food and Drug Control in Beijing, China). The chemotherapeutic drugs that were assessed were docetaxel (Purchased from Sigma-Aldrich, St. Louis, Mo., USA, Cat. No. 01885), daunorubicin, (also known as doxorubicin, Purchased from Sigma-Aldrich, St. Louis, Mo., USA), and lapatinib (Obtained from Prof. Xiaojiang Cui, Cedars-Sinai, Beverly Hills, Calif.).

The docetaxel $IC_{50}$ and docetaxel $IC_{50(WA+D)}$ were determined in the docetaxel-resistant prostate cancer lines: (i) DU145-TxR and PC3-TxR (Both lines obtained from the Department of Medicine, University of Pittsburgh and Partners Healthcare) and (ii) the docetaxel-sensitive lines, PC3 and DU145 (Purchased from ATCC, Manassas, Va., USA).

The daunorubicin $IC_{50}$ and daunorubicin $IC_{50(WA+D)}$ were determined in the daunorubicin-sensitive and -resistant myelogenous leukemia lines K562 and K562/Dox, respectively (Obtained from Prof. Kenneth Chan, Ohio State University).

The lapatinib $IC_{50}$ and lapatinib $IC_{50(WA+D)}$ were determined in the lapatinib-sensitive, HER2-positive, breast Pretreatment of the cells with wilforlide A was carried out by aspirating the media from the wells, followed by adding 50 µl of RPMI medium containing wilforlide A in concentrations of either 1.25, 2.5, or 5 µg/ml of wilforlide A, which were prepared from a 0.5 mg/ml stock solution of wilforlide A in DMSO, and incubation of the cells for two hours under conditions of 37° C. and 5% $CO_2$. At the end of the two hour pre-treatment period, 50 µl aliquots of the desired chemotherapeutic drug RPMI medium were added according to the amounts provided in Table 2.

TABLE 2

| Chemotherapeutic Drug | Drug Concentrations used to determine $IC_{50}$ | Cell Line used to determine $IC_{50}$ |
|---|---|---|
| Docetaxel | 100, 33, 10, 3.3, 1, 0.3, 0.1 (nM) | PC3 |
| Lapatinib | 20, 6.7, 2, 0.7, 0.2, 0.07, 0.02 (µM) | SkBr3 |
| Daunorubicin | 100, 33, 10, 3.3, 1, 0.3, 0.1 (µM) | K562 |

After adding the various doses of chemotherapeutic drugs, as described above, the cells were incubated for an additional 72 hours under the same temperature and atmospheric conditions used for the pre-treatment step. Following the 72 hour docetaxel treatment period, sulforhodamine B (SRB) assays were performed as described in Example 1 to quantitate living cells. Table 3 summarizes the results of the $IC_{50}$ and $IC_{50(WA+D)}$ amounts of the tested chemotherapeutic drugs.

TABLE 3

| Therapeutic Drug | Pre-Tx-amount of wilforlide A (μg/ml) | Cell Line | Drug IC$_{50}$ no pre-Tx | Drug IC$_{50}$ after wilforlide A pre-Tx | CE |
|---|---|---|---|---|---|
| docetaxel | none added | PC3 | 1.796 nM | 1.606 nM | |
| | 1.25 | PC3-TxR | 18.30 nM | 8.768 nM | 2.9 |
| | 5.0 | PC3-TxR | 20.47 nM | 5.173 nM | 3.96 |
| | 2.5 | DU-145 | >100 nM | 42.53 nM | >2.35 |
| daunorubicin | none added | K562 | 1.046 μM | | |
| | 2.5 | K562/Dox | 30.73 μM | 13.55 μM | 2.27 |
| lapatinib | none added | SkBr3 | 0.2407 μM | | |
| | 2.5 | SkBr3-TxR | 11.58 μM | 0.8859 μM | 13 |

Example 3

Figure 2A:
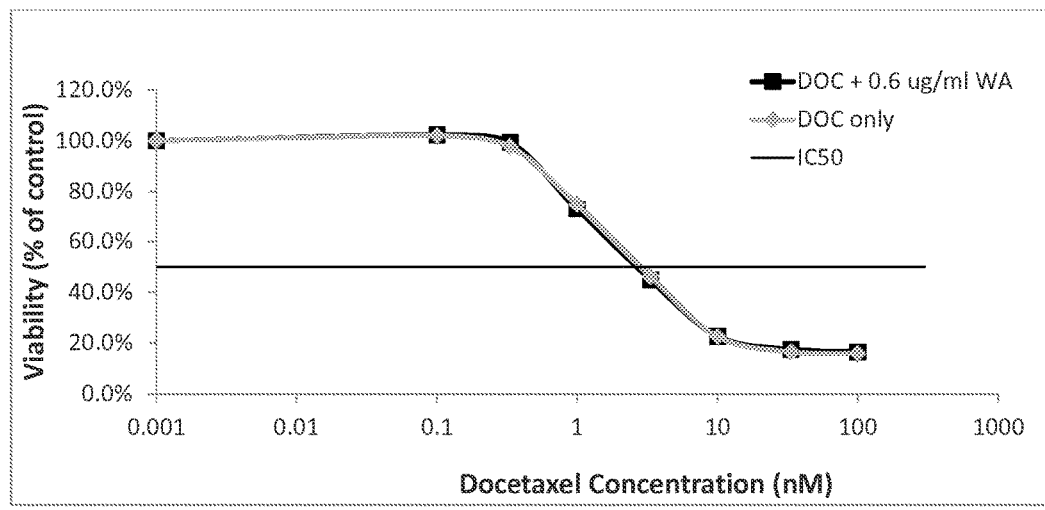
FIG. 2 shows the results of a sulforhodamine B (SRB) cell viability assay of docetaxel-sensitive PC3 cells that were pretreated with: 0.6 (FIG. 2A); 1.25 (FIG. 2B); or 2.5 (FIG. 2C) µg/ml of wilforlide A, followed by 72 hours of treatment with various concentrations of docetaxel. See Tables 4-9.
Figure 2B:
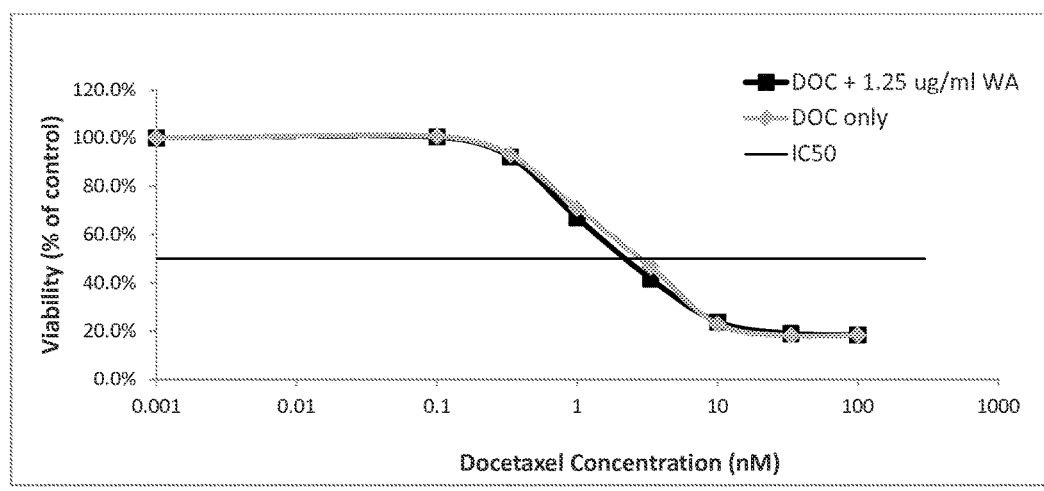
Figure 2C:
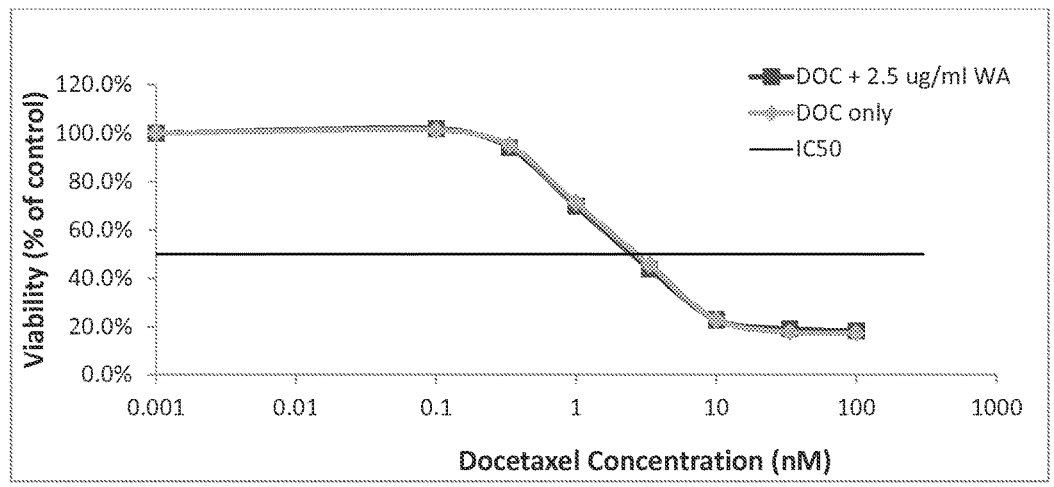
Figure 3A:
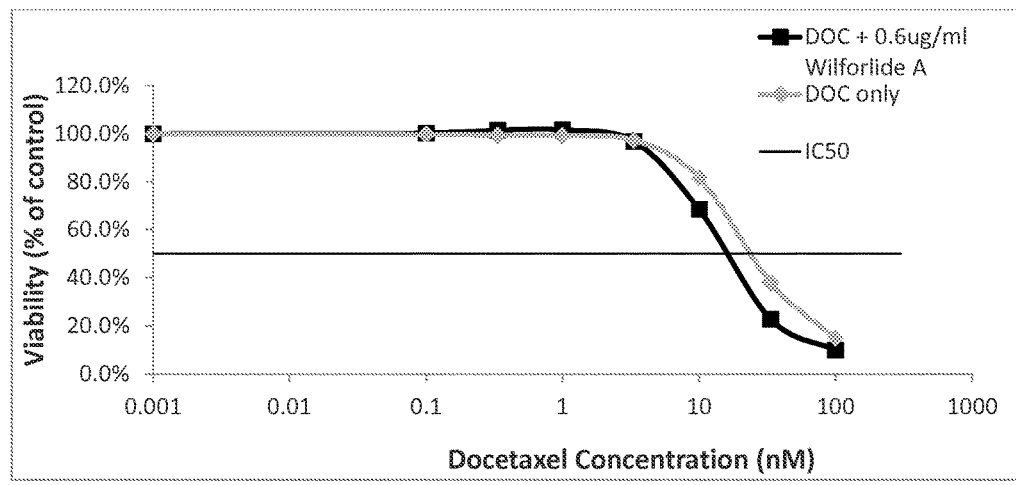
FIG. 3 shows the results of a sulforhodamine B (SRB) cell viability assay of docetaxel-resistant PC3-TxR cells that were pretreated with: 0.6 (FIG. 3A); 1.25 (FIG. 3B); 2.5 (FIG. 3C); or 5.0 (FIG. 3D) µg/ml of wilforlide A, followed by 72 hours of treatment with various concentrations of docetaxel. See Tables 10-17.
Figure 3B:
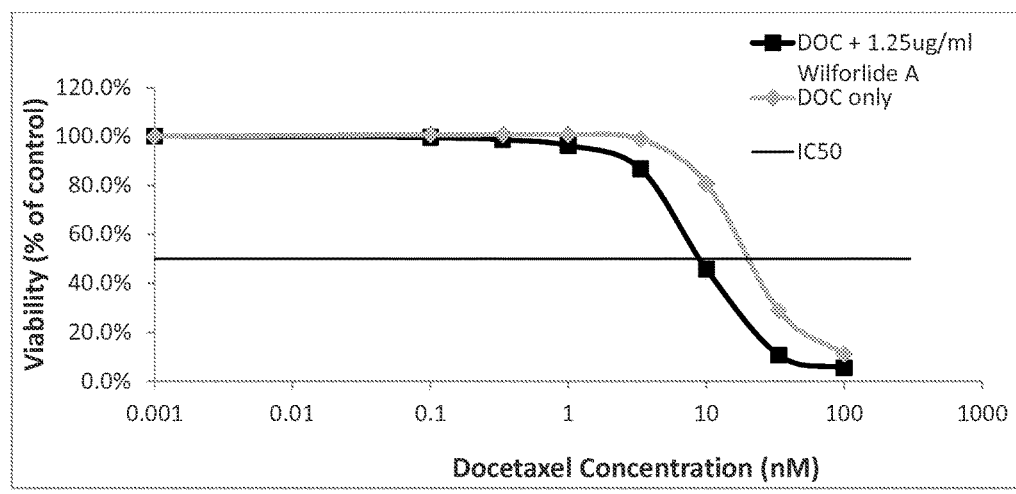
Figure 3C:
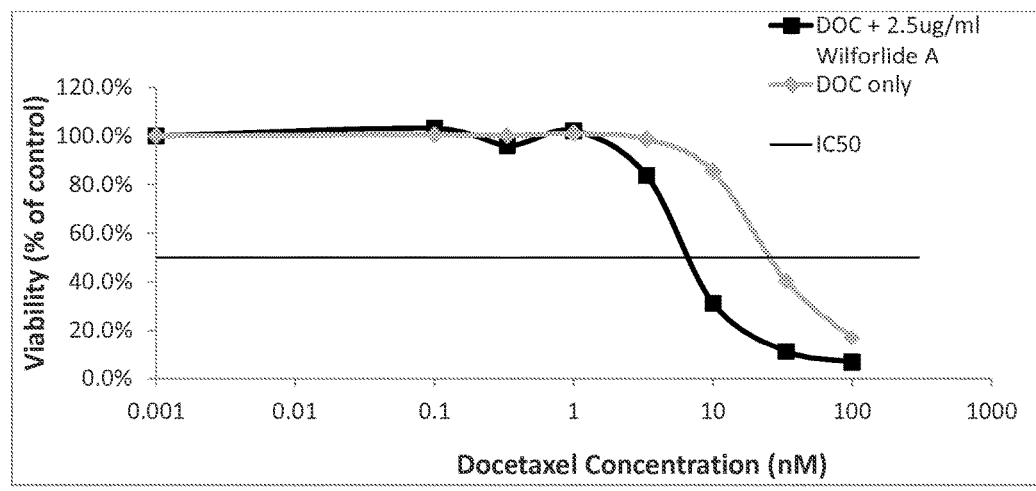
Figure 3D:
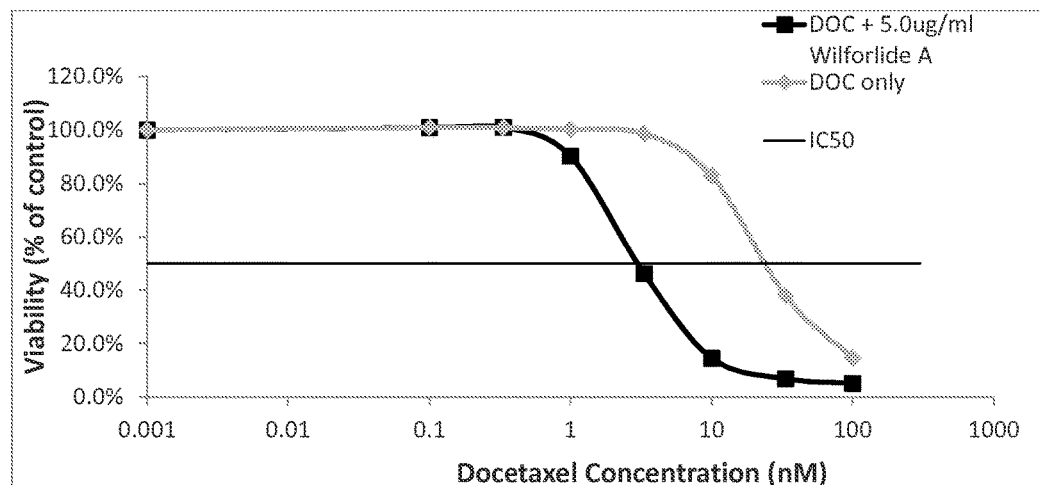

Wilforlide A pretreatment does not significantly enhance the sensitivity of docetaxel-sensitive pancreatic tumor cells to docetaxel. The chemosensitizing effect of wilforlide A pretreatment on docetaxel-treatment of PC3 cells was studied. In this study, the PC3 cells were plated in 96 well plates as described in Example 1, except that triplicate, rather than septuplicate, wells were prepared for each experimental condition. The cells were plated at passage 8. After a 24 hour rest period, the plating media were aspirated from the wells, and replaced with 50 μl of RPMI that contained 0.6, 1.25, or 2.5 μg/ml wilforlide A. The cells were then incubated for two hours at 37° C. and 5% $CO_2$. After the two hour incubation, a dose response analysis of the cells to docetaxel was performed by immediately adding 100, 33.3, 10, 3.33, 1.0, 0.333, 0.1 or 0.001 nM of docetaxel. The cells were then incubated for 72 hours at 37° C. and 5% $CO_2$. After the 72 hour incubation, sulforhodamine B (SRB) assays were performed as described in Example 1 to quantitate living cells. Tables 4, 6, and 8 report the docetaxel dose response cell viability data obtained after pre-treatment with either 0.6, 1.25, and 2.5 μg/ml wilforlide A, respectively. Tables 5, 7, and 9 report control data obtained from cells that were not pre-treated with wilforlide A prior to docetaxel treatment. FIG. 2 summarizes the data of Tables 4-9 in a graphical format.

TABLE 4

| Docetaxel (nM) | 100 | 33.3 | 10 | 3.33 | 1 | 0.333 | 0.1 | 0.001 |
|---|---|---|---|---|---|---|---|---|
| A at 565 nm | 0.290 | 0.302 | 0.408 | 0.843 | 1.303 | 1.759 | 1.855 | 1.812 |
| background = 0.043 | 0.287 | 0.323 | 0.421 | 0.814 | 1.386 | 1.804 | 1.874 | 1.840 |
| | 0.320 | 0.323 | 0.400 | 0.777 | 1.263 | 1.820 | 1.816 | 1.769 |
| mean A | 0.299 | 0.316 | 0.409 | 0.811 | 1.317 | 1.794 | 1.848 | 1.807 |
| SD | 0.018 | 0.012 | 0.011 | 0.033 | 0.063 | 0.032 | 0.030 | 0.036 |
| % viable | 16.5 | 17.5 | 22.7 | 44.9 | 72.9 | 99.3 | 102.3 | 100.0 |
| CV | 6.11 | 3.84 | 2.59 | 4.08 | 4.76 | 1.76 | 1.60 | 1.98 |

TABLE 5

| Docetaxel (nM) | 100 | 33.3 | 10 | 3.33 | 1 | 0.333 | 0.1 | 0.001 |
|---|---|---|---|---|---|---|---|---|
| A at 565 nm | 0.300 | 0.321 | 0.432 | 0.862 | 1.452 | 1.845 | 1.875 | 1.827 |
| background = 0.043 | 0.270 | 0.295 | 0.409 | 0.832 | 1.366 | 1.808 | 1.878 | 1.892 |
| | 0.311 | 0.293 | 0.404 | 0.860 | 1.306 | 1.737 | 1.875 | 1.800 |
| mean A | 0.293 | 0.303 | 0.415 | 0.851 | 1.374 | 1.796 | 1.876 | 1.839 |
| SD | 0.021 | 0.016 | 0.015 | 0.017 | 0.073 | 0.055 | 0.002 | 0.047 |
| % viable | 15.9 | 16.4 | 22.5 | 46.3 | 74.7 | 97.7 | 102.0 | 100.0 |
| CV | 7.24 | 5.16 | 3.60 | 1.97 | 5.34 | 3.06 | 0.09 | 2.57 |

TABLE 6

| Docetaxel (nM) | 100 | 33.3 | 10 | 3.33 | 1 | 0.333 | 0.1 | 0.001 |
|---|---|---|---|---|---|---|---|---|
| A at 565 nm | 0.356 | 0.364 | 0.451 | 0.853 | 1.290 | 1.828 | 1.953 | 1.923 |
| background = 0.044 | 0.350 | 0.372 | 0.466 | 0.784 | 1.291 | 1.770 | 1.949 | 1.921 |
| | 0.376 | 0.383 | 0.484 | 0.810 | 1.353 | 1.814 | 1.992 | 2.028 |
| mean A | 0.361 | 0.373 | 0.467 | 0.816 | 1.311 | 1.804 | 1.965 | 1.957 |
| SD | 0.014 | 0.010 | 0.017 | 0.035 | 0.036 | 0.030 | 0.024 | 0.061 |
| % viable | 18.4 | 19.1 | 23.9 | 41.7 | 67.0 | 92.2 | 100.4 | 100.0 |
| CV | 3.77 | 2.56 | 3.54 | 4.27 | 2.75 | 1.68 | 1.21 | 3.13 |

TABLE 7

| Docetaxel (nM) | 100 | 33.3 | 10 | 3.33 | 1 | 0.333 | 0.1 | 0.001 |
|---|---|---|---|---|---|---|---|---|
| A at 565 nm | 0.349 | 0.337 | 0.464 | 0.895 | 1.398 | 1.735 | 1.980 | 1.888 |
| background = 0.044 | 0.366 | 0.357 | 0.427 | 0.942 | 1.314 | 1.845 | 1.925 | 2.010 |
|  | 0.365 | 0.368 | 0.450 | 0.889 | 1.441 | 1.871 | 1.992 | 1.957 |
| mean A | 0.360 | 0.354 | 0.447 | 0.909 | 1.384 | 1.817 | 1.966 | 1.952 |
| SD | 0.010 | 0.016 | 0.019 | 0.029 | 0.065 | 0.072 | 0.036 | 0.061 |
| % viable | 18.4 | 18.1 | 22.9 | 46.6 | 70.9 | 93.1 | 100.7 | 100.0 |
| CV | 2.65 | 4.44 | 4.18 | 3.19 | 4.67 | 3.97 | 1.82 | 3.13 |

TABLE 8

| Docetaxel (nM) | 100 | 33.3 | 10 | 3.33 | 1 | 0.333 | 0.1 | 0.001 |
|---|---|---|---|---|---|---|---|---|
| A at 565 nm | 0.318 | 0.358 | 0.402 | 0.810 | 1.201 | 1.672 | 1.738 | 1.702 |
| background = 0.044 | 0.330 | 0.333 | 0.425 | 0.779 | 1.206 | 1.640 | 1.806 | 1.735 |
|  | 0.316 | 0.317 | 0.381 | 0.717 | 1.259 | 1.632 | 1.812 | 1.819 |
| mean A | 0.322 | 0.336 | 0.403 | 0.769 | 1.222 | 1.648 | 1.786 | 1.752 |
| SD | 0.008 | 0.021 | 0.022 | 0.047 | 0.032 | 0.021 | 0.041 | 0.060 |
| % viable | 18.4 | 19.2 | 23.0 | 43.9 | 69.8 | 94.1 | 101.9 | 100.0 |
| CV | 2.35 | 6.14 | 5.46 | 6.16 | 2.63 | 1.28 | 2.30 | 3.44 |

TABLE 9

| Docetaxel (nM) | 100 | 33.3 | 10 | 3.33 | 1 | 0.333 | 0.1 | 0.001 |
|---|---|---|---|---|---|---|---|---|
| A at 565 nm | 0.348 | 0.366 | 0.460 | 0.885 | 1.379 | 1.864 | 1.999 | 2.050 |
| background = 0.044 | 0.348 | 0.366 | 0.475 | 0.969 | 1.513 | 1.989 | 2.079 | 2.018 |
|  | 0.341 | 0.328 | 0.437 | 0.877 | 1.358 | 1.823 | 1.964 | 1.900 |
| mean A | 0.346 | 0.354 | 0.458 | 0.911 | 1.417 | 1.892 | 2.014 | 1.990 |
| SD | 0.004 | 0.022 | 0.019 | 0.051 | 0.084 | 0.086 | 0.059 | 0.079 |
| % viable | 17.4 | 17.8 | 23.0 | 45.8 | 71.2 | 95.1 | 101.2 | 100.0 |
| CV | 1.17 | 6.20 | 4.18 | 5.60 | 5.93 | 4.57 | 2.93 | 3.97 |

Example 4

Wilforlide A sensitizes the docetaxel-resistant prostate cancer cell line, PC3-TrX, to docetaxel. The chemosensitizing effect of wilforlide A pretreatment on docetaxel-treatment to PC3-TrX cells was studied. In this study, the PC3-TxR cells were plated in 96 well plates as described in Example 3. After a 24 hour rest period, the plating media were aspirated from the wells, and replaced with 50 μl of RPMI containing wilforlide A at concentrations of either 0.6, 1.25, 2.5, or 5.0 μg/ml. The cells that were plated for pre-treatment with 1.25 and 2.5 μg/ml of wilforlide A were plated at passage 37. The cells that were plated for pre-treatment with 0.6 and 5.0 μg/ml of wilforlide A were plated at passage 42. The cells were then incubated for two hours at 37° C. and 5% $CO_2$. After the two hour incubation, a dose response analysis of the cells to docetaxel was performed by immediately adding 100, 33.3, 10, 3.33, 1.0, 0.333, 0.1 or 0.001 nM of docetaxel. The cells were then incubated for 72 hours at 37° C. and 5% $CO_2$. After the 72 hour incubation, sulforhodamine B (SRB) assays were performed as described in Example 1 to quantitate living cells. Tables 10, 12, 14, and 16 report the docetaxel dose response cell viability data obtained after pre-treatment with either 0.6, 1.25, 2.5, and 5.0 μg/ml wilforlide A, respectively. Tables 11, 13, 15, and 17 report control data obtained from cells that were not pre-treated with wilforlide A prior to docetaxel treatment. FIG. 3 summarizes the data of Tables 10-17 in a graphical format.

TABLE 10

| Docetaxel (nM) | 100 | 33.3 | 10 | 3.33 | 1 | 0.333 | 0.1 | 0.001 |
|---|---|---|---|---|---|---|---|---|
| A at 565 nm | 0.266 | 0.617 | 1.810 | 2.534 | 2.648 | 2.639 | 2.578 | 2.585 |
| background = 0.044 | 0.259 | 0.574 | 1.766 | 2.498 | 2.640 | 2.630 | 2.626 | 2.612 |
|  | 0.247 | 0.582 | 1.754 | 2.519 | 2.628 | 2.638 | 2.603 | 2.594 |
| mean A | 0.257 | 0.591 | 1.777 | 2.517 | 2.639 | 2.636 | 2.602 | 2.597 |
| SD | 0.010 | 0.023 | 0.029 | 0.018 | 0.010 | 0.005 | 0.024 | 0.014 |
| % viable | 9.9 | 22.8 | 68.4 | 96.9 | 101.6 | 101.5 | 100.2 | 100.0 |
| CV | 3.74 | 3.87 | 1.66 | 0.72 | 0.38 | 0.19 | 0.92 | 0.53 |

TABLE 11

| Docetaxel (nM) | 100 | 33.3 | 10 | 3.33 | 1 | 0.333 | 0.1 | 0.001 |
|---|---|---|---|---|---|---|---|---|
| A at 565 nm | 0.396 | 1.041 | 2.159 | 2.578 | 2.638 | 2.583 | 2.590 | 2.604 |
| background = 0.044 | 0.407 | 0.958 | 2.204 | 2.547 | 2.556 | 2.620 | 2.638 | 2.597 |
|  | 0.377 | 0.963 | 2.022 | 2.479 | 2.560 | 2.572 | 2.570 | 2.614 |

TABLE 11-continued

| Docetaxel (nM) | 100 | 33.3 | 10 | 3.33 | 1 | 0.333 | 0.1 | 0.001 |
|---|---|---|---|---|---|---|---|---|
| mean A | 0.393 | 0.987 | 2.128 | 2.535 | 2.585 | 2.592 | 2.599 | 2.605 |
| SD | 0.015 | 0.047 | 0.095 | 0.051 | 0.046 | 0.025 | 0.035 | 0.009 |
| % viable | 15.1 | 37.9 | 81.7 | 97.3 | 99.2 | 99.5 | 99.8 | 100.0 |
| CV | 3.86 | 4.71 | 4.45 | 2.00 | 1.79 | 0.97 | 1.34 | 0.33 |

TABLE 12

| Docetaxel (nM) | 100 | 33.3 | 10 | 3.33 | 1 | 0.333 | 0.1 | 0.001 |
|---|---|---|---|---|---|---|---|---|
| A at 565 nm | 0.116 | 0.254 | 1.122 | 2.082 | 2.339 | 2.358 | 2.362 | 2.373 |
| background = 0.047 | 0.130 | 0.238 | 1.006 | 2.003 | 2.154 | 2.246 | 2.199 | 2.304 |
|  | 0.137 | 0.256 | 1.056 | 1.946 | 2.200 | 2.251 | 2.362 | 2.279 |
| mean A | 0.128 | 0.249 | 1.061 | 2.010 | 2.231 | 2.285 | 2.308 | 2.319 |
| SD | 0.011 | 0.010 | 0.058 | 0.068 | 0.096 | 0.063 | 0.094 | 0.049 |
| % viable | 5.5 | 10.7 | 45.8 | 86.7 | 96.2 | 98.5 | 99.5 | 100.0 |
| CV | 8.38 | 3.96 | 5.48 | 3.40 | 4.32 | 2.77 | 4.08 | 2.10 |

TABLE 13

| Docetaxel (nM) | 100 | 33.3 | 10 | 3.33 | 1 | 0.333 | 0.1 | 0.001 |
|---|---|---|---|---|---|---|---|---|
| A at 565 nm | 0.252 | 0.628 | 1.844 | 2.171 | 2.233 | 2.232 | 2.341 | 2.234 |
| background = 0.047 | 0.236 | 0.660 | 1.797 | 2.200 | 2.302 | 2.229 | 2.208 | 2.188 |
|  | 0.246 | 0.629 | 1.699 | 2.178 | 2.139 | 2.214 | 2.120 | 2.205 |
| mean A | 0.245 | 0.639 | 1.780 | 2.183 | 2.225 | 2.225 | 2.223 | 2.209 |
| SD | 0.008 | 0.018 | 0.074 | 0.015 | 0.082 | 0.010 | 0.111 | 0.023 |
| % viable | 11.1 | 28.9 | 80.6 | 98.8 | 100.7 | 100.7 | 100.6 | 100.0 |
| CV | 3.31 | 2.85 | 4.16 | 0.69 | 3.68 | 0.43 | 5.01 | 1.05 |

TABLE 14

| Docetaxel (nM) | 100 | 33.3 | 10 | 3.33 | 1 | 0.333 | 0.1 | 0.001 |
|---|---|---|---|---|---|---|---|---|
| A at 565 nm | 0.186 | 0.305 | 0.793 | 2.112 | 2.691 | 2.193 | 2.751 | 2.555 |
| background = 0.046 | 0.172 | 0.273 | 0.808 | 2.188 | 2.594 | 2.598 | 2.613 | 2.574 |
|  | 0.161 | 0.288 | 0.801 | 2.155 | 2.580 | 2.602 | 2.582 | 2.573 |
| mean A | 0.173 | 0.289 | 0.801 | 2.152 | 2.622 | 2.464 | 2.649 | 2.567 |
| SD | 0.013 | 0.016 | 0.008 | 0.038 | 0.060 | 0.235 | 0.090 | 0.011 |
| % viable | 6.7 | 11.2 | 31.2 | 83.8 | 102.1 | 96.0 | 103.2 | 100.0 |
| CV | 7.24 | 5.55 | 0.94 | 1.77 | 2.31 | 9.54 | 3.40 | 0.42 |

TABLE 15

| Docetaxel (nM) | 100 | 33.3 | 10 | 3.33 | 1 | 0.333 | 0.1 | 0.001 |
|---|---|---|---|---|---|---|---|---|
| A at 565 nm | 0.412 | 1.049 | 2.203 | 2.608 | 2.657 | 2.588 | 2.638 | 2.656 |
| background = 0.046 | 0.472 | 1.046 | 2.285 | 2.606 | 2.637 | 2.658 | 2.648 | 2.609 |
|  | 0.443 | 1.086 | 2.241 | 2.555 | 2.661 | 2.638 | 2.632 | 2.607 |
| mean A | 0.442 | 1.060 | 2.243 | 2.590 | 2.652 | 2.628 | 2.639 | 2.624 |
| SD | 0.030 | 0.022 | 0.041 | 0.030 | 0.013 | 0.036 | 0.008 | 0.028 |
| % viable | 16.9 | 40.4 | 85.5 | 98.7 | 101.1 | 100.2 | 100.6 | 100.0 |
| CV | 6.78 | 2.10 | 1.83 | 1.16 | 0.48 | 1.37 | 0.31 | 1.06 |

TABLE 16

| Docetaxel (nM) | 100 | 33.3 | 10 | 3.33 | 1 | 0.333 | 0.1 | 0.001 |
|---|---|---|---|---|---|---|---|---|
| A at 565 nm | 0.120 | 0.168 | 0.372 | 1.052 | 2.079 | 2.334 | 2.274 | 2.300 |
| background = 0.046 | 0.118 | 0.156 | 0.325 | 0.986 | 2.072 | 2.316 | 2.366 | 2.326 |

TABLE 16-continued

| Docetaxel (nM) | 100 | 33.3 | 10 | 3.33 | 1 | 0.333 | 0.1 | 0.001 |
|---|---|---|---|---|---|---|---|---|
| | 0.116 | 0.147 | 0.308 | 1.153 | 2.100 | 2.341 | 2.345 | 2.295 |
| mean A | 0.118 | 0.157 | 0.335 | 1.064 | 2.084 | 2.330 | 2.328 | 2.307 |
| SD | 0.002 | 0.011 | 0.033 | 0.084 | 0.015 | 0.013 | 0.048 | 0.017 |
| % viable | 5.1 | 6.8 | 14.5 | 46.1 | 90.3 | 101.0 | 100.9 | 100.0 |
| CV | 1.69 | 6.70 | 9.89 | 7.91 | 0.70 | 0.55 | 2.07 | 0.72 |

TABLE 17

| Docetaxel (nM) | 100 | 33.3 | 10 | 3.33 | 1 | 0.333 | 0.1 | 0.001 |
|---|---|---|---|---|---|---|---|---|
| A at 565 nm | 0.393 | 0.964 | 2.069 | 2.591 | 2.623 | 2.644 | 2.637 | 2.603 |
| background = 0.046 | 0.387 | 0.908 | 2.204 | 2.554 | 2.612 | 2.607 | 2.607 | 2.596 |
| | 0.363 | 1.078 | 2.191 | 2.547 | 2.582 | 2.617 | 2.629 | 2.598 |
| mean A | 0.381 | 0.983 | 2.155 | 2.564 | 2.606 | 2.623 | 2.624 | 2.599 |
| SD | 0.016 | 0.087 | 0.074 | 0.024 | 0.021 | 0.019 | 0.016 | 0.004 |
| % viable | 14.7 | 37.8 | 82.9 | 98.7 | 100.3 | 100.9 | 101.0 | 100.0 |
| CV | 4.16 | 8.81 | 3.46 | 0.92 | 0.81 | 0.73 | 0.59 | 0.14 |

Example 5

Figure 4:
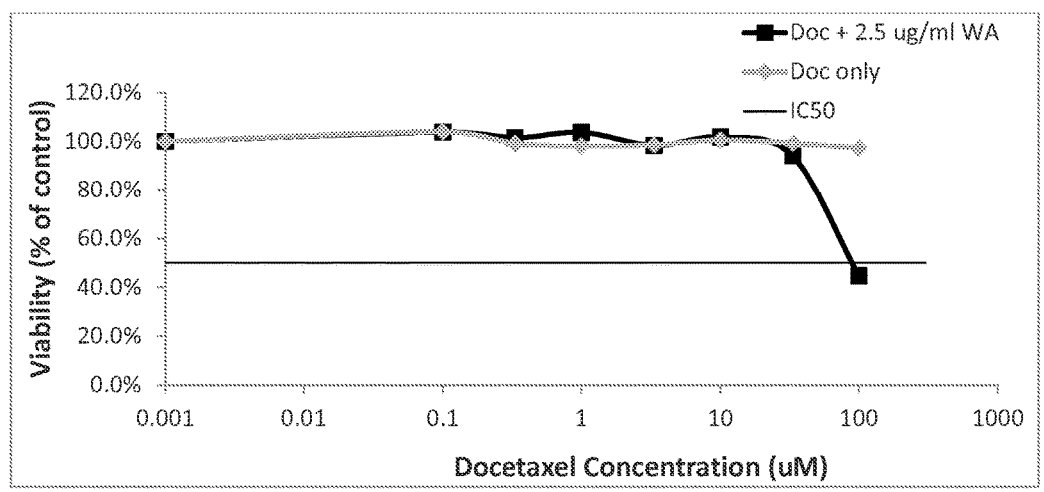
FIG. 4 shows the results of a sulforhodamine B (SRB) cell viability assay of docetaxel-resistant DU145-TxR cells that were pretreated with 2.5 µg/ml of wilforlide A, followed by 72 hours of treatment with various concentrations of docetaxel. See Tables 18-19.

Wilforlide A sensitizes the docetaxel-resistant prostate cancer cell line, DU145-Txr, to docetaxel. The chemosensitizing effect of wilforlide A pretreatment on docetaxel-treatment to DU145-Txr cells was studied. In this study, the DU145-Txr cells were plated in 96 well plates as described for PC3 cells in Example 3. After a 24 hour rest period, the plating media were aspirated from the wells, and replaced with either 50 µl of RPMI that contained either 0 or 2.5 µg/ml of wilforlide A. The cells were then incubated for two hours at 37° C. and 5% $CO_2$. After the two hour incubation, a dose response analysis of the cells to docetaxel was performed by immediately adding 100, 33.3, 10, 3.33, 1.0, 0.333, 0.1 or 0.001 nM of docetaxel. The cells were then incubated for 72 hours at 37° C. and 5% $CO_2$. After the 72 hour incubation, sulforhodamine B (SRB) assays were performed as described in Example 1 to quantitate living cells. Table 18 reports the docetaxel dose response cell viability data obtained after pre-treatment with 2.5 µg/ml wilforlide A, and Table 19 reports the control data obtained from cells that were not pre-treated with wilforlide A prior to docetaxel treatment. FIG. 4 summarizes the data of Tables 18 and 19 in a graphical format.

TABLE 18

| Docetaxel (nM) | 100 | 33.3 | 10 | 3.33 | 1 | 0.333 | 0.1 | 0.001 |
|---|---|---|---|---|---|---|---|---|
| A at 565 nm | 0.987 | 2.086 | 2.171 | 2.064 | 2.177 | 2.187 | 2.248 | 2.092 |
| background = 0.046 | 0.926 | 2.018 | 2.204 | 2.090 | 2.229 | 2.102 | 2.263 | 2.151 |
| | 0.957 | 1.930 | 2.155 | 2.155 | 2.246 | 2.218 | 2.151 | 2.170 |
| mean A | 0.956 | 2.011 | 2.176 | 2.103 | 2.217 | 2.169 | 2.220 | 2.137 |
| SD | 0.031 | 0.078 | 0.025 | 0.047 | 0.036 | 0.060 | 0.061 | 0.041 |
| % viable | 44.7 | 94.1 | 101.8 | 98.4 | 103.7 | 101.5 | 103.9 | 100.0 |
| CV | 3.19 | 3.89 | 1.15 | 2.23 | 1.62 | 2.77 | 2.74 | 1.90 |

TABLE 19

| Docetaxel (nM) | 100 | 33.3 | 10 | 3.33 | 1 | 0.333 | 0.1 | 0.001 |
|---|---|---|---|---|---|---|---|---|
| A at 565 nm | 2.153 | 2.145 | 2.254 | 2.207 | 2.279 | 2.281 | 2.354 | 2.285 |
| background = 0.046 | 2.224 | 2.270 | 2.359 | 2.230 | 2.233 | 2.251 | 2.413 | 2.199 |
| | 2.217 | 2.303 | 2.203 | 2.236 | 2.137 | 2.175 | 2.272 | 2.289 |
| mean A | 2.198 | 2.239 | 2.272 | 2.224 | 2.216 | 2.235 | 2.346 | 2.257 |
| SD | 0.039 | 0.083 | 0.080 | 0.015 | 0.072 | 0.055 | 0.071 | 0.051 |
| % viable | 97.4 | 99.2 | 100.6 | 98.5 | 98.2 | 99.0 | 103.9 | 100.0 |
| CV | 1.78 | 3.72 | 3.50 | 0.69 | 3.27 | 2.44 | 3.02 | 2.25 |

Example 6

Figure 5:
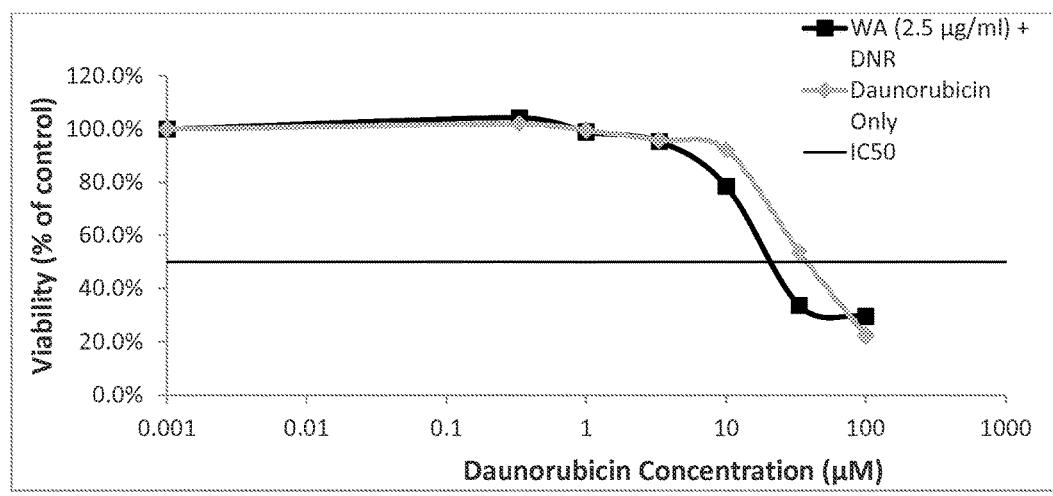
FIG. 5 shows the results of a sulforhodamine B (SRB) cell viability assay of daunorubicin-resistant K562/Dox cells that were pretreated with 2.5 µg/ml of wilforlide A, followed by 72 hours of treatment with various concentrations of daunorubicin. See Tables 20-21.

Wilforlide A sensitizes the daunorubicin-resistant myelogenous leukemia line K562/Dox, to daunorubicin. The chemosensitizing effect of wilforlide A pretreatment on daunorubicin-treatment to K562/Dox cells was studied. In this study, the K562/Dox cells were plated in 96 well plates as described for PC3 cells in Example 3, except that 5000 thousand rather than 3000 cells were plated per well. After a 24 hour rest period, the plating media were aspirated from the wells, and replaced with either 50 μl of RPMI that contained 0 or 2.5 μg/ml of wilforlide A. The cells were then incubated for two hours at 37° C. and 5% $CO_2$. After the two hour incubation, a dose response analysis of the cells to daunorubicin was performed by immediately adding 100, 33.3, 10, 3.33, 1.0, 0.333, 0.1 or 0.001 μM of daunorubicin. The cells were then incubated for 72 hours at 37° C. and 5% $CO_2$. After the 72 hour incubation, sulforhodamine B (SRB) assays were performed as described in Example 1 to quantitate living cells. Table 20 reports the daunorubicin dose response cell viability data obtained after pre-treatment with 2.5 μg/ml wilforlide A, and Table 21 reports the control data obtained from cells that were not pre-treated with wilforlide A prior to daunorubicin treatment. FIG. 5 summarizes the data of Tables 20 and 21 in a graphical format.

Example 7

Figure 6:
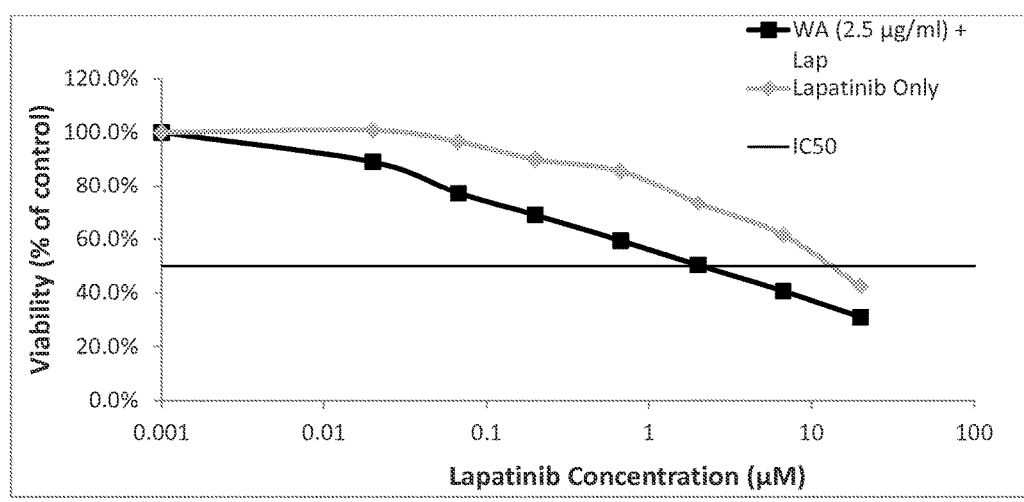
FIG. 6 shows the results of a sulforhodamine B (SRB) cell viability assay of lapitinib-resistant, HER2-positive, breast adenocarcinoma SkBr3-TxR cells that were pretreated with 2.5 µg/ml of wilforlide A, followed by 72 hours of treatment with various concentrations of daunorubicin. See Tables 22-23.

Wilforlide A sensitizes the lapitinib-resistant, HER2-positive, breast adenocarcinoma line SkBr3-TxR, to lapitinib. The chemosensitizing effect of wilforlide A pretreatment lapatinib-treatment to SkBr3-Txr cells was studied. In this study, the SkBr3-Txr cells were plated in 96 well plates as described for PC3 cells in Example 3, with the exception that 5000, rather than 3000 cells were plated per well. After a 24 hour rest period, the plating media were aspirated from the wells, and replaced with either 50 μl of RPMI that contained wilforlide A at a concentration of 2.5 μg/ml, or did not contain wilforlide A at all. The cells were then incubated for two hours at 37° C. and 5% $CO_2$. After the two hour incubation, a dose response analysis of the cells to lapatinib was performed by immediately adding 20, 6.7, 2.0, 0.67, 0.2, 0.067, 0.002, and 0.001 μM of lapatinib in 50 μl RPMI aliquots to the designated wells. The cells were then incubated for 72 hours at 37° C. and 5% $CO_2$. After the 72 hour incubation, sulforhodamine B (SRB) assays were performed as described in Example 1 to quantitate living cells. Table 22 reports the docetaxel dose response cell viability data obtained after pre-treatment with 2.5 μg/ml wilforlide A, and Table 23 reports the control data obtained from cells that were not pre-treated with wilforlide A prior to lapatinib treatment. FIG. 6 summarizes the data of Tables 22 and 23 in a graphical format.

TABLE 20

| Daunorubicin (μM) | 100 | 33.3 | 10 | 3.33 | 1 | 0.333 | 0.1 | 0.001 |
|---|---|---|---|---|---|---|---|---|
| A at 565 nm | 0.843 | 1.016 | 2.200 | 2.657 | 2.777 | 2.838 | 0.492 | 2.797 |
| background = 0.043 | 0.815 | 0.901 | 2.392 | 2.681 | 2.784 | 2.951 | 1.520 | 2.838 |
|  | 0.840 | 0.926 | 2.049 | 2.715 | 2.799 | 3.025 | 2.556 | 2.810 |
| mean A | 0.832 | 0.947 | 2.213 | 2.684 | 2.786 | 2.938 | 1.522 | 2.815 |
| SD | 0.015 | 0.060 | 0.172 | 0.029 | 0.011 | 0.094 | 1.032 | 0.021 |
| % viable | 29.6 | 33.7 | 78.6 | 95.4 | 99.0 | 104.4 | 54.1 | 100.0 |
| CV | 1.85 | 6.38 | 7.77 | 1.09 | 0.40 | 3.21 | 67.79 | 0.74 |

TABLE 21

| Daunorubicin (μM) | 100 | 33.3 | 10 | 3.33 | 1 | 0.333 | 0.1 | 0.001 |
|---|---|---|---|---|---|---|---|---|
| A at 565 nm | 0.757 | 1.625 | 2.678 | 2.805 | 2.892 | 2.943 | 1.477 | 2.848 |
| background = 0.043 | 0.657 | 1.639 | 2.720 | 2.780 | 2.878 | 2.956 | 0.864 | 2.923 |
|  | 0.528 | 1.406 | 2.613 | 2.741 | 2.872 | 2.955 | 2.705 | 2.909 |
| mean A | 0.647 | 1.556 | 2.670 | 2.775 | 2.880 | 2.951 | 1.682 | 2.893 |
| SD | 0.115 | 0.131 | 0.054 | 0.032 | 0.010 | 0.007 | 0.937 | 0.040 |
| % viable | 22.4 | 53.8 | 92.3 | 95.9 | 99.6 | 102.0 | 58.1 | 100.0 |
| CV | 17.74 | 8.40 | 2.02 | 1.16 | 0.36 | 0.25 | 55.75 | 1.38 |

TABLE 22

| Lapatinib (μM) | 20 | 6.7 | 2.0 | 0.67 | 0.2 | 0.067 | 0.01 | 0.001 |
|---|---|---|---|---|---|---|---|---|
| A at 565 nm | 0.731 | 0.794 | 0.987 | 1.127 | 1.299 | 1.344 | 1.817 | 2.186 |
| background = 0.051 | 0.673 | 0.932 | 1.095 | 1.398 | 1.540 | 1.909 | 1.976 | 2.285 |
|  | 0.706 | 1.040 | 1.339 | 1.517 | 1.854 | 1.992 | 2.256 | 2.323 |
| mean A | 0.703 | 0.922 | 1.140 | 1.347 | 1.564 | 1.748 | 2.016 | 2.265 |
| SD | 0.029 | 0.123 | 0.180 | 0.200 | 0.278 | 0.353 | 0.222 | 0.071 |
| % viable | 31.1 | 40.7 | 50.4 | 59.5 | 69.1 | 77.2 | 89.0 | 100.0 |
| CV | 4.14 | 13.37 | 15.81 | 14.83 | 17.79 | 20.17 | 11.02 | 3.12 |

TABLE 23

| Lapatinib (μM) | 20 | 6.7 | 2.0 | 0.67 | 0.2 | 0.067 | 0.01 | 0.001 |
|---|---|---|---|---|---|---|---|---|
| A at 565 nm | 0.958 | 1.426 | 1.609 | 1.871 | 1.945 | 2.142 | 2.458 | 2.348 |
| background = 0.051 | 1.024 | 1.445 | 1.759 | 1.990 | 2.081 | 2.261 | 2.246 | 2.297 |
|  | 0.957 | 1.384 | 1.708 | 2.048 | 2.186 | 2.264 | 2.261 | 2.260 |
| mean A | 0.980 | 1.418 | 1.692 | 1.970 | 2.071 | 2.222 | 2.322 | 2.302 |
| SD | 0.038 | 0.031 | 0.076 | 0.090 | 0.121 | 0.070 | 0.118 | 0.044 |
| % viable | 42.6 | 61.6 | 73.5 | 85.6 | 90.0 | 96.6 | 100.9 | 100.0 |
| CV | 3.92 | 2.20 | 4.51 | 4.58 | 5.84 | 3.13 | 5.10 | 1.92 |

Example 8

Figure 7A:
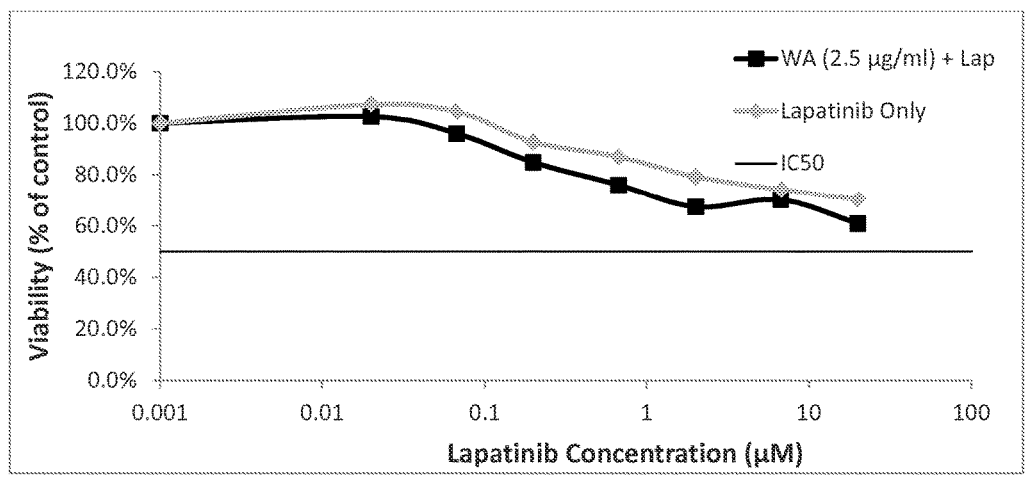
FIG. 7 shows the results of a sulforhodamine B (SRB) cell viability assay of lapitinib-resistant, HER2-positive, breast ductal carcinoma Bt474-TxR cells that were pretreated with 2.5 (FIG. 7A) or 25 (FIG. 7B) µg/ml of wilforlide A, followed by 72 hours of treatment with various concentrations of daunorubicin. See Tables 24-27
Figure 7B:
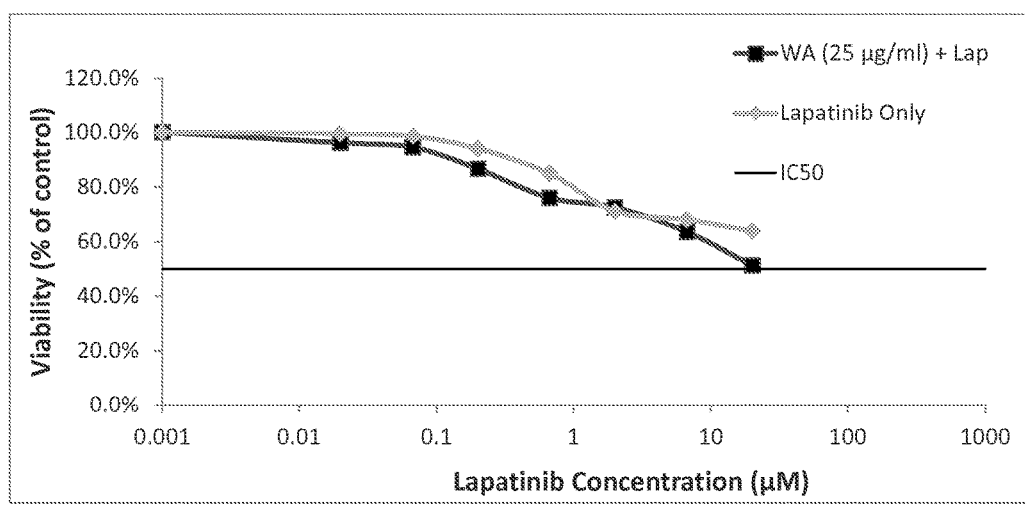

Wilforlide A sensitizes the lapitinib-resistant, HER2-positive breast ductal carcinoma line BT474-TxR, to lapatinib. The chemosensitizing effect of wilforlide A pretreatment lapatinib-treatment to Bt474-Txr cells was studied. In this study, the Bt-474-Txr cells were plated in 96 well plates as described for PC3 cells in Example 3, with the exception that 5000, rather than 3000 cells were plated per well. After a 24 hour rest period, the plating media were aspirated from the wells, and replaced with either 50 μl of RPMI that contained 0, 2.5 or 25 μg/ml of wilforlide A. The cells were then incubated for two hours at 37° C. and 5% $CO_2$. After the two hour incubation, a dose response analysis of the cells to lapatinib was performed by immediately adding 20, 6.7, 2.0, 0.67, 0.2, 0.067, 0.002, and 0.001 μM of lapatinib in 50 μl RPMI aliquots to the designated wells. The cells were then incubated for 72 hours at 37° C. and 5% $CO_2$. After the 72 hour incubation, sulforhodamine B (SRB) assays were performed as described in Example 1 to quantitate living cells. Tables 24 and 26 report the lapatinib dose response cell viability data obtained after pre-treatment with 2.5 and 25 μg/ml wilforlide A, respectively, and Tables 25 and 27 report the control data obtained from cells that were not pre-treated with wilforlide A prior to lapatinib treatment. FIG. 7 summarizes the data of Tables 24-27 in a graphical format.

TABLE 24

| Lapatinib (μM) | 20 | 6.7 | 2.0 | 0.67 | 0.2 | 0.067 | 0.01 | 0.001 |
|---|---|---|---|---|---|---|---|---|
| A at 565 nm | 0.798 | 0.947 | 0.895 | 1.000 | 1.103 | 1.224 | 1.309 | 1.301 |
| background = 0.045 | 0.689 | 0.814 | 0.791 | 0.898 | 0.990 | 1.110 | 1.203 | 1.109 |
|  | 0.817 | 0.893 | 0.861 | 0.975 | 1.114 | 1.297 | 1.368 | 1.370 |
| mean A | 0.768 | 0.884 | 0.849 | 0.957 | 1.069 | 1.210 | 1.293 | 1.260 |
| SD | 0.069 | 0.067 | 0.053 | 0.053 | 0.069 | 0.094 | 0.084 | 0.135 |
| % viable | 60.9 | 70.2 | 67.4 | 76.0 | 84.8 | 96.1 | 102.6 | 100.0 |
| CV | 9.00 | 7.56 | 6.25 | 5.55 | 6.42 | 7.79 | 6.47 | 10.74 |

TABLE 25

| Lapatinib (μM) | 20 | 6.7 | 2.0 | 0.67 | 0.2 | 0.067 | 0.01 | 0.001 |
|---|---|---|---|---|---|---|---|---|
| A at 565 nm | 0.911 | 0.926 | 1.014 | 1.091 | 1.159 | 1.320 | 1.352 | 1.272 |
| background = 0.045 | 0.914 | 1.027 | 0.996 | 1.160 | 1.196 | 1.343 | 1.344 | 1.341 |
|  | 0.803 | 0.823 | 0.951 | 1.003 | 1.116 | 1.249 | 1.318 | 1.128 |
| mean A | 0.876 | 0.925 | 0.987 | 1.084 | 1.157 | 1.304 | 1.338 | 1.247 |
| SD | 0.063 | 0.102 | 0.032 | 0.079 | 0.040 | 0.049 | 0.018 | 0.109 |
| % viable | 70.2 | 74.2 | 79.1 | 87.0 | 92.8 | 104.6 | 107.3 | 100.0 |
| CV | 7.22 | 11.03 | 3.29 | 7.26 | 3.46 | 3.76 | 1.33 | 8.72 |

TABLE 26

| Lapatinib (μM) | 20 | 6.7 | 2.0 | 0.67 | 0.2 | 0.067 | 0.01 | 0.001 |
|---|---|---|---|---|---|---|---|---|
| A at 565 nm | 0.530 | 0.663 | 0.876 | 0.813 | 0.991 | 1.124 | 1.173 | 1.216 |
| background = 0.047 | 0.655 | 0.737 | 0.831 | 0.937 | 0.963 | 1.101 | 1.062 | 1.161 |
|  | 0.577 | 0.787 | 0.789 | 0.865 | 1.028 | 1.032 | 1.076 | 1.066 |
| mean A | 0.587 | 0.729 | 0.832 | 0.872 | 0.994 | 1.086 | 1.104 | 1.148 |
| SD | 0.063 | 0.062 | 0.044 | 0.062 | 0.033 | 0.048 | 0.060 | 0.076 |
| % viable | 51.2 | 63.5 | 72.5 | 76.0 | 86.6 | 94.6 | 96.2 | 100.0 |
| CV | 10.75 | 8.56% | 5.23 | 7.14 | 3.28 | 4.41 | 5.48 | 6.61 |

TABLE 27

| Lapatinib (μM) | 20 | 6.7 | 2.0 | 0.67 | 0.2 | 0.067 | 0.01 | 0.001 |
|---|---|---|---|---|---|---|---|---|
| A at 565 nm | 0.807 | 0.866 | 0.887 | 1.024 | 1.176 | 1.236 | 1.151 | 1.096 |
| background = 0.047 | 0.697 | 0.798 | 0.809 | 0.955 | 1.096 | 1.195 | 1.192 | 1.071 |
|  | 0.735 | 0.722 | 0.797 | 1.004 | 1.028 | 1.032 | 1.149 | 1.069 |
| mean A | 0.746 | 0.795 | 0.831 | 0.994 | 1.100 | 1.154 | 1.164 | 1.170 |
| SD | 0.056 | 0.072 | 0.049 | 0.036 | 0.074 | 0.108 | 0.024 | 0.015 |
| % viable | 63.8 | 68.0 | 71.0 | 85.0 | 94.0 | 98.7 | 99.5 | 100.0 |
| CV | 7.48 | 9.06 | 5.88 | 3.57 | 6.73 | 9.35 | 2.08 | 1.29 |

Example 9

Wilforlide A is an effective chemosensitizor for docetaxel in vivo. Based on the results, above, that showed wilforlide A to be a chemosensitizer for docetaxel in vitro, in vivo studies were conducted using CD-1 mice (Charles River Laboratories International Inc. Wilmington, Mass.) to assess the effectiveness of orally-administered wilforlide A on the chemotherapeutic effect of docetaxel. Maximum tolerated dose (MTD)s of wilforlide A were determined for single MTD (sdMTD) and multiple dose MTD (mdMTD) protocols. The MTD was defined as the dose: 1) that was nonfatal; ii) caused no more than a 10% retardation of body weight gain as compared to control animals; and 3) did not cause overt organ dysfunction or side effects. A seven day-long sdMTD study was performed in which the single dose was administered on day one. A seven day-long mdMTD study was also performed in which wilforlide was administered daily.

The administration routes used in these studies were intravenous (i.v.), oral gavage (p.o.), and intraperitoneal (i.p.) administration. Because wilforlide A is poorly water soluble, it was dissolved in either dimethyl sulfoxide (DMSO, Sigma-aldrich, St. Louis, Mo.), Capmul™ MCM C8 EP (mono/diglycerides of caprylic acid, ABITEC, Columbus, Ohio), or hydropropyl β cyclodextrin (HBCD, Roquette America, Keokuk, Iowa). More specifically, working concentrations of wilforlide A were prepared by: (i) dissolving wilforlide A inDMSO at a concentration of 3 mg/ml at 80° C. for use with i.p. administration; (ii) dissolving wilforlide A in Capmul™ at a concentration of 3 mg/ml for use with p.o. administration; and (iii) dissolving wilforlide A inDMSO at a concentration of 1.5 mg/ml at 80° C., and then diluted ten times in 40% HBCD (w/v) for use with i.v. administration. Due to the poor solubility of wilforlide A, the maximum dose that can be achieved is around 6, 30, and 1.2 mg/kg for i.p., p.o., and i.v. respectively. Thus, the MTD study was started with these doses.

For each dose regimen tested, 12 CD-1 mice (6 males and 6 females) received appropriate volume of each wilforlide A preparation. The mice were housed with food and water ad libitum. All mice were monitored for the four hour period that immediately followed wilforlide A administration for indications of acute toxicity, as well as monitored at least 3 times daily for one week for indications of delayed toxicity. The mice were also weighed 24 hours post treatment as well as every other day during the week-long study. The results showed that the mice were all well tolerant at doses of 6, 30, and 1.2 mg/kg for i.p., p.o., and i.v. respectively for both single and multiple dose regimens. Based on these results, no additional lower doses were tested and these doses were utilized in subsequent pharmacokinetic and xenograft studies.

Figure 8A:
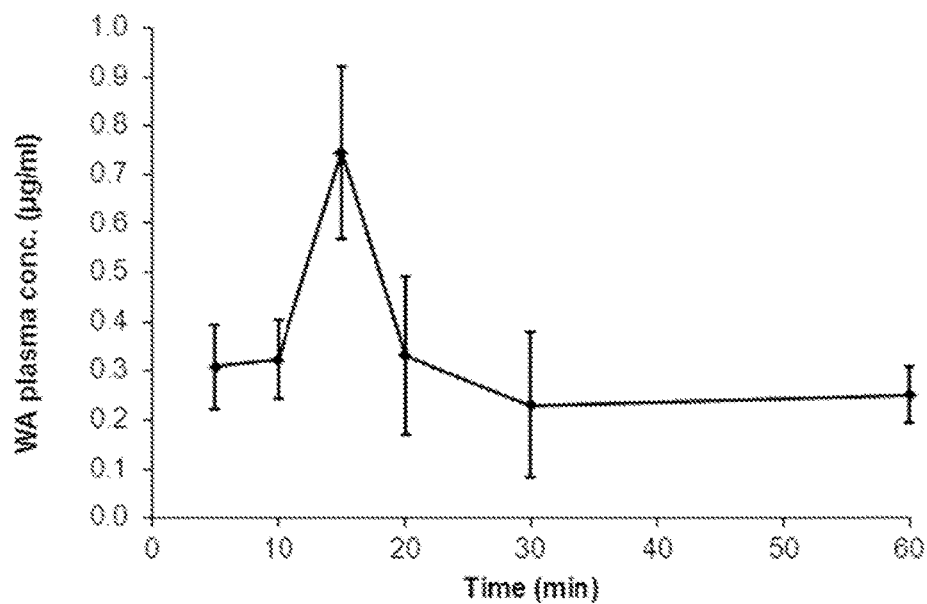
FIG. 8 shows the plasma concentration time course curves following the (FIG. 8A) i.p., (FIG. 8B) p.o., and (FIG. 8C) i.v. administrations of wilforlide A to CD-1 mice.
Figure 8B:
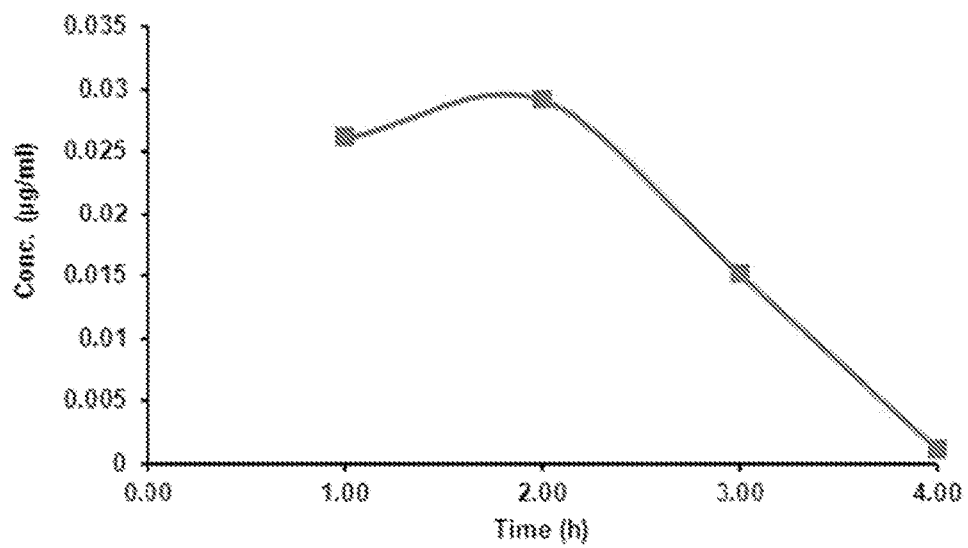
Figure 8C:
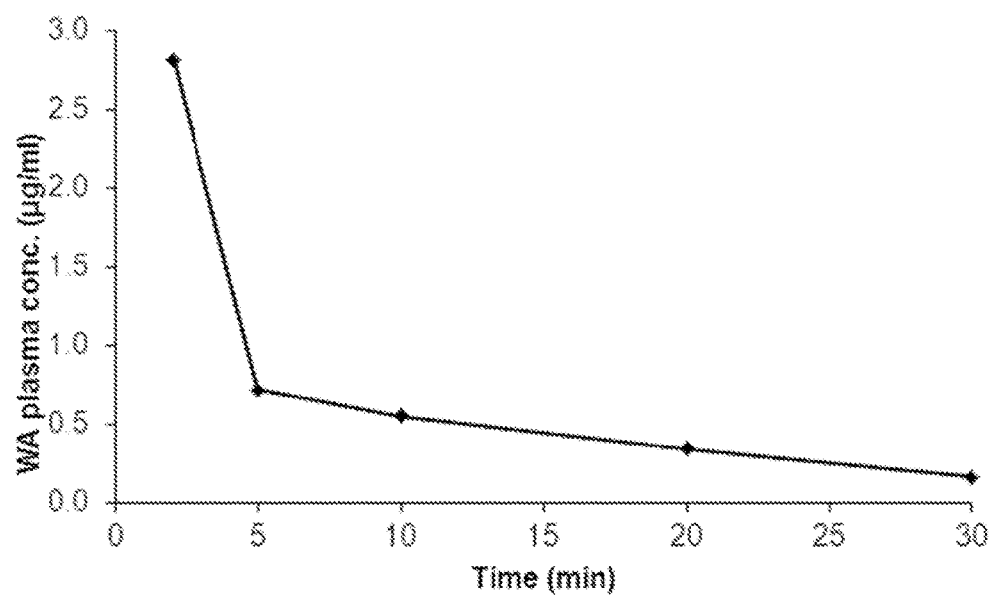

To determine the pharmacokinetics of wilforlide A in mice, wilforlide A was formulated for i.p., p.o., and i.v. administration as describe above, for doses of 6, 30, and 1.2 mg/kg, respectively. Four CD-1 mice were sacrificed prior to wilforlide A administration and at: (i) 5, 10, 15, 20, 30, and 60 min after i.p. administration; (ii) 2, 5, 10, 15, 20, and 30 min after p.o. administration; and (iii) 1, 2, 3, and 4 hours after i.v. administration. At each time point, blood was drawn via heart puncture and plasma was separated by a five min centrifution at 10000 rpm. Plasma wilforlide A concentrations were measured using a validated HPLC-MS/MS method. The peak drug concentration ($C_{max}$) and time to peak drug concentration ($T_{max}$) were read directly from the plasma concentration time course data, while the terminal elimination half-life ($T_{1/2}$) was calculated to be 0.693/Ke, where Ke was the terminal phase elimination rate. The plasma concentration time course curves following i.p., p.o., and i.v. are shown in FIG. 8. A-C, respectfully. The wilforlide A $C_{max}$ values following i.p., p.o., and i.v., administration were 0.75, 0.03, and 2.82 μg/ml, respectively, with corresponding $T_{1/2}$ times of 41.0, 25.6 and 11.2 min. Based on these results, p.o. administration was shown not to be able to achieve a reasonable plasma concentration and thus was not included in the subsequent in vivo xenograft study.

An in vivo tumor xenograft study was performed to assess the chemosensitizating effect, with respect to docetaxel, of i.p. and i.v.-administered wilforlide A on docetaxel-resistant human prostate cancer tumors caused by xenotransplantation of PC3-TxR cells. Briefly, wilforlide A was formulated and administered by i.v. and i.p. routes as described above, and administered in combination with docetaxel, which was i.v.-administered at a dose of 20 mg/kg. Tumor sizes at the end of a 14 day time course were compared to tumor sizes in host mice that received only docetaxel. To perform this study, tumors were caused to form in fifty six severe four to six week-old, severe combined immunodeficient (SCID) male mice (Taconic Farms, Inc. Oxnard, Calif.) that weighed from 15 to 20 g were obtained and housed in cages with HEPA-filtered air (12-hr light/dark cycle) by subcutaneously injecting PC3-TxR cells in the mice. To prepare the cells for injection, the cells were suspended in a 1:1 mixture of Matrigel (BC Biosciences, Franklin Lakes, N.J., U.S.A.) and RPMI 1640 (Mediatech, Manassas, Va., or Life Technologies, Grand Island, N.Y.). Then the cells were subcutaneously implanted into planks of mice via injection. Mice that had consistently shown tumor growth for fourteen days following the injection of cells were used in the tumor studies. More specifically, these studies were initiated when the xenografted tumors reached a tumor size of about 120 mm$^3$, calculated by the formula for a semiepplipoid, i.e., Volume=Width2×(Length/2).

Figure 9:
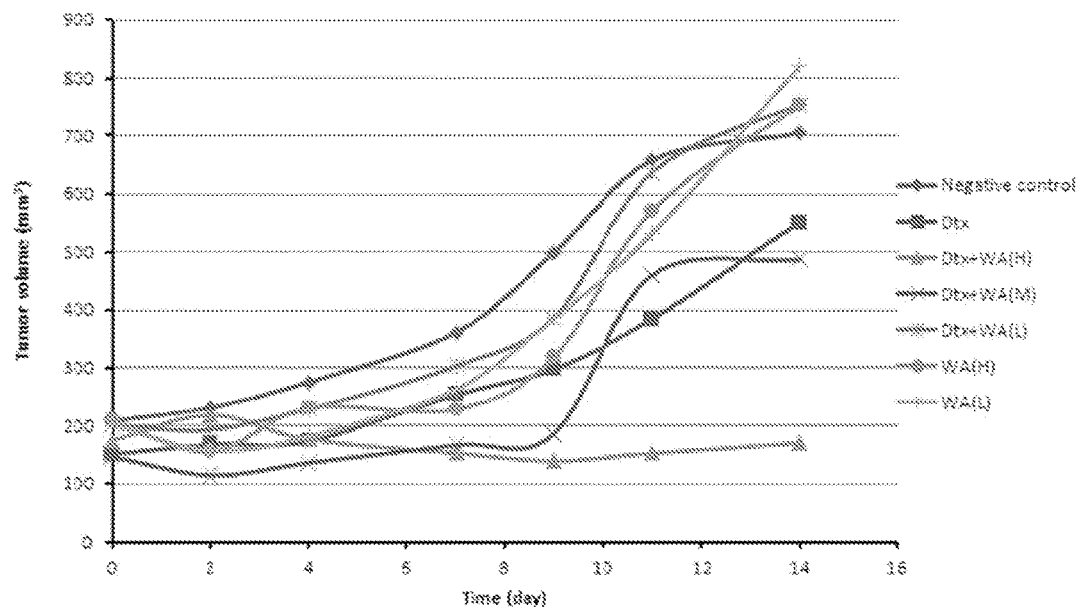
FIG. 9 shows the chemosensitizing effects to docetaxel-resistant human PC3-TxR cell tumors that are hosted by SCID mice, where the mice receive various amounts of wilforlide A over the course of a 15 day-long docetaxel-treatment period, as described in Example 9.

The tumor-containing mice in the study were randomized into 7 groups according to their treatments as follows: Group (1) no treatment (i.e., negative control); Group (2) i.v.-administered docetaxel (20 mg/kg) once a week; Group (3) i.v.-administered docetaxel (20 mg/kg) once a week plus i.v.-administered wilforlide A (1.2 mg/kg) once a week, immediately after docetaxel administration plus i.p.-administered wilforlide A (6 mg/kg) once daily; Group (4) i.v.-administered docetaxel (20 mg/kg) once a week plus i.v.-administered wilforlide A (0.6 mg/kg) once a week immediately after docetaxel administration plus i.p.-administered wilforlide A (3 mg/kg) once daily; Group (5) i.v.-administered docetaxel (20 mg/kg) once a week plus i.v.-administered wilforlide A (0.3 mg/kg) once a week immediately after docetaxel administration plus i.p.-administered wilforlide A (1.5 mg/kg) once daily; Group (6) i.v.-administered wilforlide A (1.2 mg/kg) once a week plus i.p.-administered wilforlide A (6 mg/kg) once daily; and Group (7) i.p.-administered wilforlide A (0.3 mg/kg) once a week plus i.p.-administered wilforlide A (1.5 mg/kg) once daily. Changes in tumor volumes in response to the aforementioned conditions are shown in FIG. 9. The treatment protocol of Group (3) showed a significant retardation of tumor growth compared to other groups. Wilforlide A itself did not significantly inhibit the tumor growth, but wilforlide A significantly enhanced docetaxel's anti-tumor effect.

REFERENCES

Huang Y, and Sadee W. (2003). Drug sensitivity and resistance genes in cancer chemotherapy: a chemogenomics approach. Drug Discov Today 8, 356-363.

Huang Y, et al. (2005). Correlating gene expression with chemical scaffolds of cytotoxic agents: ellipticines as substrates and inhibitors of MDR1. Pharmacogenomics J 5, 112-125.

Makarovskiy, A N et al. (2002). Survival of docetaxel-resistant prostate cancer cells in vitro depends on phenotype alterations and continuity of drug exposure. Cell Mol Life Sci 59, 1198-1211.

Salzberg M, et al. (2007). An open-label, noncomparative phase II trial to evaluate the efficacy and safety of docetaxel in combination with gefitinib in patients with hormone-refractory metastatic prostate cancer, Onkologie 30, 355-360.

Seruga B., et al. (2010). Drug resistance in metastatic castration-resistant prostate cancer. Nat Rev Clin Oncol.

Singh A, et al. (2010). Expression of ABCG2 (BCRP) is regulated by Nrf2 in cancer cells that confers side population and chemoresistance phenotype. Mol Cancer Ther 9, 2365-2376.

Sirotnak F M, et al. (2000). Efficacy of cytotoxic agents against human tumor xenografts is markedly enhanced by coadministration of ZD1839 (Iressa), an inhibitor of EGFR tyrosine kinase. Clin Cancer Res 6, 4885-4892.

Wang Z., et al. (2010). Transporter-mediated multidrug resistance and its modulation by Chinese medicines and other herbal products. Curr Drug Discovery Technologies 1:54-56

The claimed invention is:

1. A method of treating a patient suffering from a prostate tumor, wherein tumor cells have acquired resistance to docetaxel, the method comprising administering a sensitizing agent consisting of an amount of wilforlide A to the patient, wherein the administered amount of wilforlide A is sufficient to sensitize the docetaxel-resistant tumor cells to the anti-tumor growth effect of docetaxel.

2. The method according to claim 1, wherein the administered amount of docetaxel is 75 mg/m$^2$ docetaxel, and wherein the amount of docetaxel is administered at least once every three weeks for one to ten three week cycles.

3. The method according to claim 1, wherein the amount of wilforlide A is administered prior to administration of the docetaxel.

4. The method according to claim 1, wherein the amount of wilforlide A is co-administered with docetaxel.

5. The method according to claim 1, wherein the amount of wilforlide A is formulated for intravenous administration, and, wherein the intravenous formulation comprises wilforlide A at a concentration of from 50 to 500 µg/ml.

* * * * *